(12) United States Patent
Johannessen et al.

(10) Patent No.: US 12,723,227 B2
(45) Date of Patent: Sep. 1, 2026

(54) SYSTEMS AND METHODS FOR RECYCLING GAS IN REACTORS

(71) Applicant: Gas 2 Feed AS, Farsund (NO)

(72) Inventors: Arild Johannessen, Sandnes (NO); Terje Ernst Mikalsen, Osteras (NO)

(73) Assignee: Gas 2 Feed AS, Farsund (NO)

( * ) Notice: Subject to any disclaimer, the term of this patent is extended or adjusted under 35 U.S.C. 154(b) by 713 days.

(21) Appl. No.: 18/057,011

(22) Filed: Nov. 18, 2022

(65) Prior Publication Data

US 2023/0159874 A1 May 25, 2023

Related U.S. Application Data

(60) Provisional application No. 63/281,550, filed on Nov. 19, 2021.

(51) Int. Cl.
*C12M 1/04* (2006.01)
*C12M 1/34* (2006.01)

(52) U.S. Cl.
CPC ............ *C12M 27/04* (2013.01); *C12M 41/34* (2013.01)

(58) Field of Classification Search
None
See application file for complete search history.

(56) References Cited

U.S. PATENT DOCUMENTS 3,776,531 A * 12/1973 Ebner ................. B01F 23/2331 261/87
4,290,885 A * 9/1981 Kwak ..................... C02F 3/207 210/197
4,978,616 A 12/1990 Dean et al.
7,579,163 B2 8/2009 Eriksen et al.
10,538,730 B2 1/2020 Nguyen et al.
(Continued)

FOREIGN PATENT DOCUMENTS

CA 2181312 A1 * 1/1997 ........ B01F 23/23354
CN 85109440 A * 7/1987
(Continued)

OTHER PUBLICATIONS

PCT International Searching Authority; International Search Report and Written Opinion for Application No. PCT/IB2022/061 mailed Feb. 24, 2023; 14 pages.
(Continued)

*Primary Examiner* — William H. Beisner
(74) *Attorney, Agent, or Firm* — Merchant & Gould P.C.

(57) ABSTRACT

The present disclosure provides systems and methods for recycling gas in a reactor. An example of gas-recycling system comprises: a housing, a gas conduit, and a powered propeller. The housing encloses a gas space and a liquid space, wherein the gas space is configured to collect gas within a reactor. The powered propeller comprises a shaft having an upper end and a lower end; and a plurality of radial blades connected to the lower end of the shaft. Upon rotation of the powered propeller, the powered propeller is configured to: generate a suction to cause the collected gas to flow from the gas space to the liquid space through the conduit; cause fluid of the reactor to flow in a direction from the upper end of the shaft to the lower end of the shaft; and mix the liquid and the collected gas proximate the powered propeller.

21 Claims, 10 Drawing Sheets

(56) References Cited

U.S. PATENT DOCUMENTS

| | | | | |
|---|---|---|---|---|
| 2013/0065285 | A1 * | 3/2013 | Sefton | C12M 29/06 435/135 |
| 2013/0189763 | A1 * | 7/2013 | Dalla-Betta | C12N 1/20 435/286.1 |
| 2013/0273637 | A1 | 10/2013 | Griffiths et al. | |
| 2018/0245108 | A1 * | 8/2018 | Reed | C12P 7/54 |
| 2020/0318054 | A1 | 10/2020 | Cuello et al. | |

FOREIGN PATENT DOCUMENTS

| | | | | |
|---|---|---|---|---|
| DE | 9201820 | U1 * | 5/1992 | |
| EP | 0027912 | A1 * | 5/1981 | B01F 23/23353 |
| WO | 03016460 | A1 | 2/2003 | |
| WO | 2017218978 | A1 | 12/2017 | |

OTHER PUBLICATIONS

Chilean Examiner's Report including Notification, Search Report, and Expert Report for Application No. 202401494 mailed Jan. 9, 2026, Machine Translations included, 34 pages.

* cited by examiner 100
114
115
110
112
111
116
101
109
102
103
106
106
Gas Flow
121
123
105
104
G
120
111
107
160
162
161
161
Fluid Flow
113
122
125
125
117
130
131
131
124
124
118
108

114
100'
115
110'
112
116
111
101
109
106
106
102
103
Gas
Flow
121
140
105
120
120
123
160
162
161
161
Fluid
Flow
133'
130'
132'
131'
131'
125
117
130
131'
134'
124
124
118
108

110
114
200
205
100
116
101
106
106
103
120
104
160
161
203
107
130
124
124
206
204
118
202
202
$CO_2$
$O_2$
$H_2$
201

300
301
306
304
305
302
303
100
205
117
106
106
101
105
Fluid Flow
203
206
202
202
201
$H_2$
$O_2$
$CO_2$ 301
306
400
304
302
303
117
100
110
150
D1
D2
α
202
$H_2$
$O_2$
$CO_2$
201
403
410
401
402
151
152
404
Fluid Flow
203
206

Figure 7:
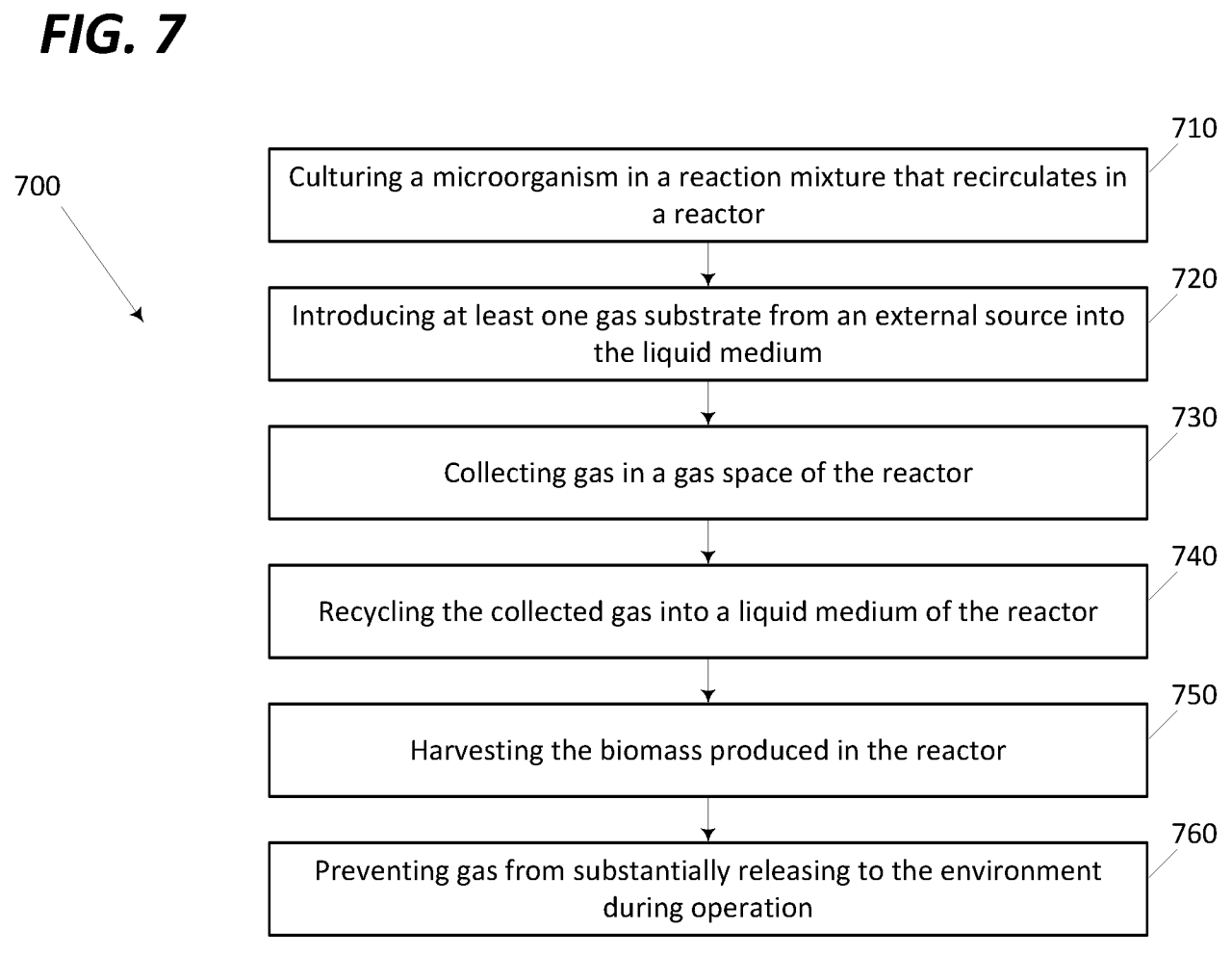

710 Culturing a microorganism in a reaction mixture that recirculates in a reactor 720 Introducing at least one gas substrate from an external source into the liquid medium 730 Collecting gas in a gas space of the reactor 740 Recycling the collected gas into a liquid medium of the reactor 750 Harvesting the biomass produced in the reactor 760 Preventing gas from substantially releasing to the environment during operation

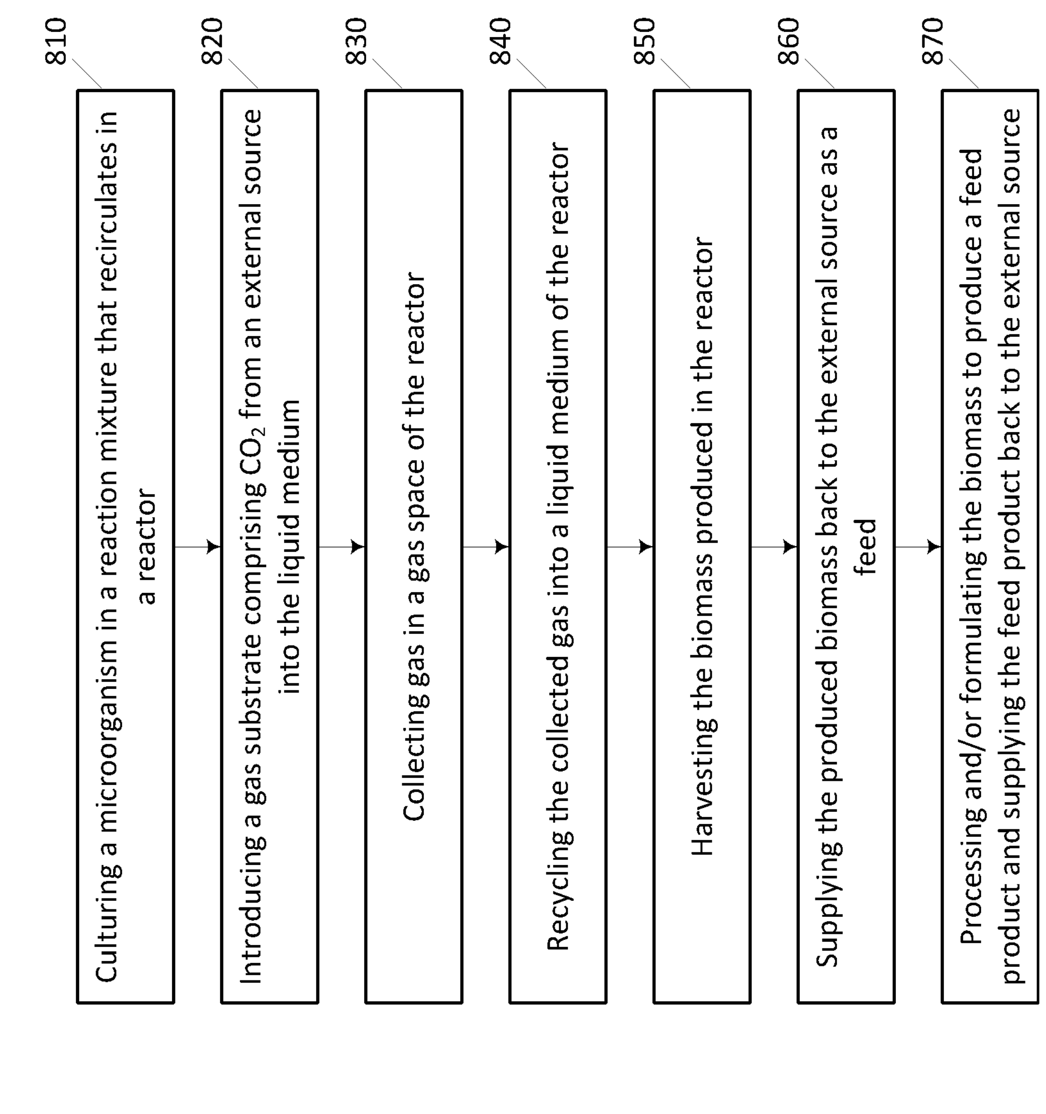
FIG. 8
800
810
Culturing a microorganism in a reaction mixture that recirculates in a reactor
820
Introducing a gas substrate comprising $CO_2$ from an external source into the liquid medium
830
Collecting gas in a gas space of the reactor
840
Recycling the collected gas into a liquid medium of the reactor
850
Harvesting the biomass produced in the reactor
860
Supplying the produced biomass back to the external source as a feed
870
Processing and/or formulating the biomass to produce a feed product and supplying the feed product back to the external source

SYSTEMS AND METHODS FOR RECYCLING GAS IN REACTORS

CROSS-REFERENCE TO RELATED APPLICATION(S)

This application claims priority to and the benefit of U.S. Provisional Patent Application No. 63/281,550, filed on Nov. 19, 2021, the disclosure of which is hereby incorporated by reference in its entirety.

BACKGROUND

Bioreactors like fermentors and fermentation processes are widely used for cultivation of microorganisms and production of useful biomasses from the microorganisms. In many conventional fermentation processes, gaseous substrates, such as air, are introduced into a fermentor and mixed with microorganisms and other ingredients in a liquid medium in the fermentor. The fermentor is operated to maintain a reaction condition for the microorganisms to convert the nutrients and gaseous substrates into biomass.

There are a number of drawbacks associated with conventional stirred tank fermentors when gases such as hydrogen, oxygen, and carbon dioxide are used as the sole energy and/or carbon source. Most unconsumed gas within the fermentors is eventually released out of the fermentors as a waste without recovery or reuse. For example, for fermentation processes that involve use of hydrogen as an input gas, hydrogen is often from an expensive feedstock, and therefore direct relief of the unconsumed hydrogen out of the fermentors significantly reduces the yield and increases the cost.

In addition, due to the low solubility of many gas substrates in liquid, the fermentation process involves a heterogenous (multi-phase) mixture of gas and liquid in the fermentor. The gas must be dissolved in the water to pass across the cell membrane of the microorganism. Pressure and high agitation and shear forces are traditionally used to promote mass transfer efficiency of gas with liquid. However, use of high agitation may break the cell wall of the microorganism and undermine the fermentation productivity. Further, many fermentation processes generate substantial by-products, in particular carbon dioxide ($CO_2$) within the fermentor. The $CO_2$ by-product without proper handling may become a burden to the environment.

SUMMARY

In general terms, this disclosure is directed to a scalable gaseous fermentation system with high gas mass transfer including recycling of gases, reactors implementing the gas-recycling system, and processes for recycling gas in a reactor or a system, and processes for biomass production.

In one aspect, the present disclosure provides to a gas-recycling system for recycling gas in a reactor. In one example, a gas-recycling system comprises: a gas-recycling system for recycling gas in a reactor, the gas-recycling system comprising: a housing, a powered propeller, and a gas conduit. The housing encloses an internal space comprising a gas space and a liquid space, wherein the gas space is configured to collect gas separated from the liquid space within a reactor. The powered propeller comprises: a shaft having an upper end and a lower end, wherein the lower end extends into the liquid space; and a plurality of radial blades connected to the lower end of the shaft. The gas conduit extends from a first end to a second end, wherein the first end is in gas communication with the gas space, and wherein the second end is proximate the radial blades and extending into the liquid space. Upon rotation of the powered propeller, the powered propeller is configured to: generate a suction to cause the collected gas to flow from the gas space to the liquid space through the conduit; cause fluid of the reactor to flow in a direction from the upper end of the shaft to the lower end of the shaft; and mix the liquid and the collected gas proximate the radial blades.

In some embodiments, the reactor is a tank reactor.

In some embodiments, a lower portion of the housing is in connection with an upstream end of a loop section external to the housing, an upper portion of the housing is in connection with a downstream end of the loop section, and the reactor causes fluid therein to flow from the lower portion of the liquid space to the upper portion of the liquid space through the loop section. In some embodiments, the loop section further comprises a plurality of static mixers configured to promote the mixing of the gas into the liquid medium.

In some embodiments, the gas conduit is within the housing, and a part of the shaft extends through an interior space of the conduit.

In some embodiments, the gas conduit is external to the housing, and the gas-recycling system further comprises an gas compressor connected to the gas conduit, the gas compressor configured to promote gas flow from the gas space to the liquid space.

In some embodiments, the gas-recycling system further comprises a liquid pump placed in the liquid space, wherein the liquid pump is configured to increase or maintain pressure and flow direction of the liquid in the reactor. In some embodiments, the liquid pump comprises an a plurality of propeller blades connected to the powered propeller above the lower end of the shaft, wherein the propeller blades are configured to co-rotate conjunctively with the shaft during operation.

In some embodiments, the liquid space contains a reaction mixture comprising: a substrate comprising $CO_2$, $H_2$, $O_2$, and optionally $N_2$; and a liquid medium comprising a microorganism capable of converting the substrate into biomass.

In some embodiments, the microorganism is a knallgas microorganism selected from the group consisting of: *Rhodopseudomonas* sp., *Rhodospirillum* sp., *Rhodococcus*; sp., *Rhizobium* sp.: *Thiocapsa* sp., *Pseudomonas* sp., *Nocardia* sp., *Hydrogenomonas* sp., *Hydrogenobacter* sp., *Hydrogenovibrio* sp.: *Helicobacter* sp., *Xanthobacter* sp., *Hydrogenophaga* sp., *Bradyrhizobium* sp., *Ralstonia* sp., *Gordonia* sp.: *Mycobacteria* sp., *Alcaligenes* sp.: *Cupriavidus* sp.: *Variovorax* sp., *Acidovorax* sp., *Anabaena* sp.: *Scenedesmus* sp.: *Chlamydomonas* sp., *Ankistrodesmus* sp., *Rhaphidium* sp., *and combinations thereof.*

In some embodiments, wherein the reactor further comprises one or more inlets configured to introduce $CO_2$, $H_2$, $O_2$, $N_2$ or any combinations thereof into the reactor.

In some embodiments, the gas-recycling system further comprises a controller configured to adjust the ratio of the $CO_2/H_2/O_2/N_2$ being introduced into the reactor.

In some embodiments, the reactor further comprises an exit port configured to harvest the produced biomass from the reactor.

In some embodiments, the external $CO_2$ gas being introduced into the reactor is from a source of biogenic $CO_2$. In some embodiments, the sources of biogenic $CO_2$ comprise an aquatic farming plant, wherein the biogenic $CO_2$ is produced by living aquatic organisms therein. In some embodiments, the sources of biogenic $CO_2$ comprises a fermentation plant, wherein the biogenic $CO_2$ is produced by fermentation microorganisms therein. In some embodiments, the produced biomass from the reactor is supplied to the aquatic farming plant or the fermentation plant as feed or energy source to the living animals or microorganisms.

In some embodiments, the biogenic $CO_2$ recirculates in the reactor without substantial emission to the environment during operation.

In another aspect, the present disclosure provides a tank reactor comprising the gas-recycling system described herein. In one example, a tank reactor comprises: a housing, a powered propeller, and a gas conduit. The housing encloses an internal space comprising a gas space and a liquid space, wherein the gas space is configured to collect gas separated from the liquid space within a reactor. The powered propeller comprises: a shaft having an upper end and a lower end, wherein the lower end extends into the liquid space; and a plurality of radial blades connected to the lower end of the shaft. The gas conduit extends from a first end to a second end, wherein the first end is in gas communication with the gas space, and wherein the second end is proximate the radial blades and extending into the liquid space. Upon rotation of the powered propeller, the powered propeller is configured to: generate a suction to cause the collected gas to flow from the gas space to the liquid space through the conduit; cause fluid of the reactor to flow in a direction from the upper end of the shaft to the lower end of the shaft; and mix the liquid and the collected gas proximate the radial blades.

In yet another aspect, the present disclosure provides a loop reactor comprising the gas-recycling system described herein. In one example, a loop reactor comprises: a housing, a powered propeller, a gas conduit, and a loop section. The housing encloses an internal space comprising a gas space and a liquid space, wherein the gas space is configured to collect gas separated from the liquid space within a reactor. The powered propeller comprises: a shaft having an upper end and a lower end, wherein the lower end extends into the liquid space; and a plurality of radial blades connected to the lower end of the shaft. The gas conduit extends from a first end to a second end, wherein the first end is in gas communication with the gas space, and wherein the second end is proximate the radial blades and extending into the liquid space. The loop section is external to the housing, wherein the loop section comprises: an upstream end connected to a lower portion of the housing; and a downstream end connected to an upper portion of the housing. Upon rotation of the powered propeller, the powered propeller is configured to: generate a suction to cause the collected gas to flow from the gas space to the liquid space through the conduit; cause fluid of the reactor to flow in a direction from the upper end of the shaft to the lower end of the shaft; mix the liquid and the collected gas proximate the radial blades. The loop reactor causes fluid therein to flow from the lower portion of the liquid space to the upper portion of the liquid space through the loop section.

In a further aspect, the present disclosure provides a process for recycling gas in a reactor comprising the gas-recycling system described herein. In one example, a process comprises: collecting gas in the gas space within the housing of the reactor; rotating the powered propeller to: generate a suction to cause the collected gas to flow from the gas space to the liquid space through the conduit; cause fluid of the reactor to flow in a direction from the upper end of the shaft to the lower end of the shaft; and mix the liquid and the collected gas proximate the radial blades.

In another aspect, the present disclosure provides a process for producing biomass through use of the reactor described herein. In one example, a process comprises: (1) culturing a microorganism in a reaction mixture in a reactor, wherein the reaction mixture comprises a liquid medium, wherein the microorganism is capable of converting $CO_2$ into biomass; (2) introducing a substrate from an external source into the liquid medium and mixing the substrate with the liquid medium, wherein the substrate comprises $CO_2$, $H_2$, $O_2$, and optionally $N_2$; (3) recycling gas separated from a liquid space back into the liquid space within the reactor, wherein the reactor comprises: a housing enclosing an internal space comprising a gas space and a liquid space; a powered propeller comprising: a shaft having an upper end and a lower end, wherein the lower end extends into the liquid space; and a plurality of radial blades connected to the lower end of the shaft; and a gas conduit extending from a first end to a second end, wherein the first end is in gas communication with the gas space, and wherein the second end is proximate the radial blades and extending into the liquid space; (4) collecting gas separated from the liquid space in the gas space within the housing; (5) rotating the powered propeller to: generate a Venturi suction to cause the collected gas to flow from the gas space to the liquid space through the conduit; cause fluid of the reactor to flow in a direction from the upper end of the shaft to the lower end of the shaft; and mix the liquid and the collected gas proximate the powered propeller; and (6) harvesting the biomass produced from the reactor.

In some embodiments, the $CO_2$ introduced into the reactor is recycled therein, without substantial emission to atmosphere during operation.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

Non-limiting embodiments of the present disclosure will be described by way of example with reference to the accompanying figures, which are schematic and are not intended to be drawn to scale. For purposes of clarity, not every component is labeled in every figure, nor is every component of each embodiment of the present disclosure shown where illustration is not necessary to allow those of ordinary skill in the art to understand the teachings of the present disclosure. In the figures:

FIG. 7 illustrates a flow diagram of one example method for producing biomass.

FIG. 8 illustrates a flow diagram of one example method 800 for recycling $CO_2$ and producing biomass from $CO_2$.

DETAILED DESCRIPTION

Figure 1A:
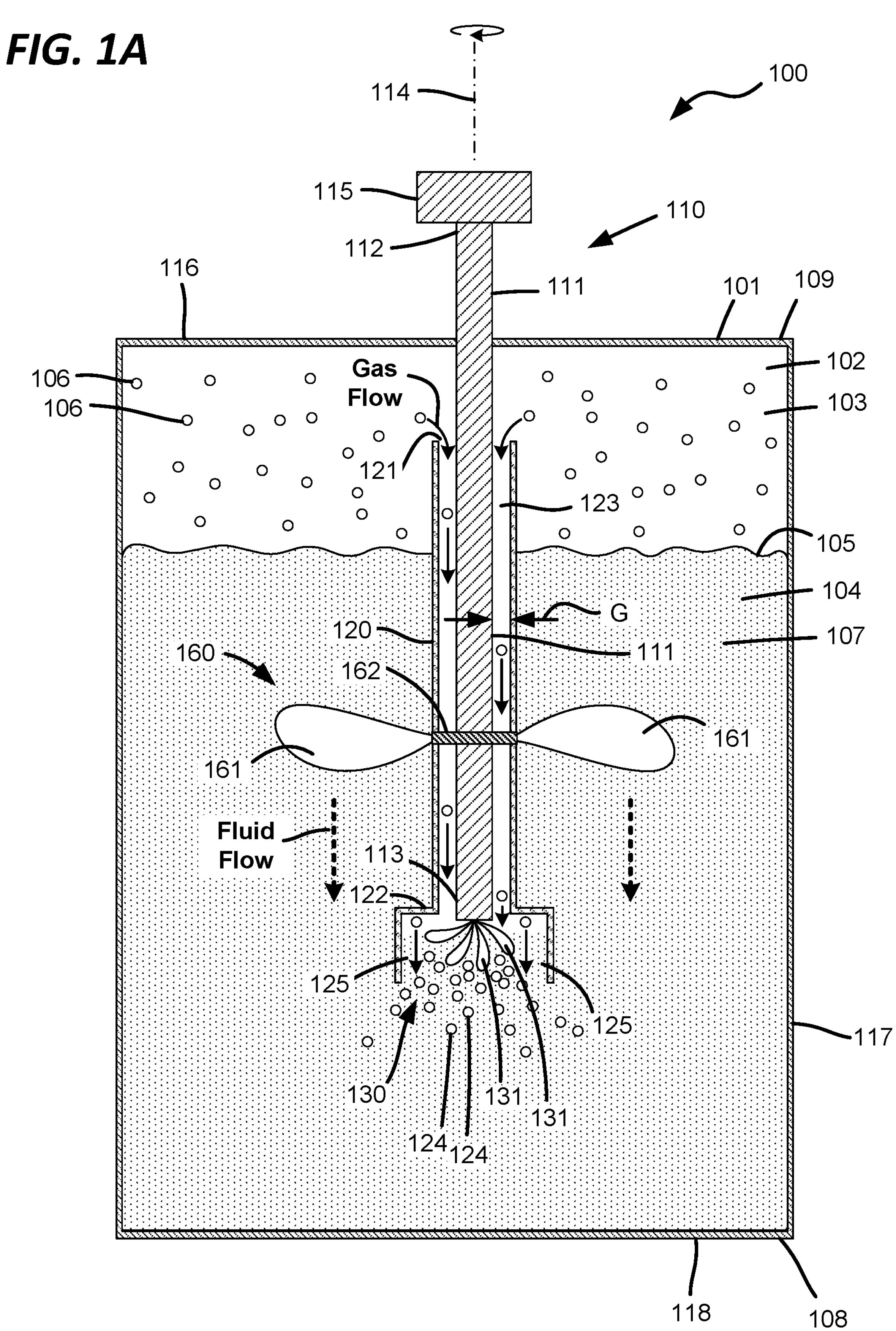
FIG. 1A illustrates a schematic view of one example gas-recycling system 100.

Various embodiments will be described in detail with reference to the drawings, wherein like reference numerals represent like parts and assemblies. Reference to various embodiments does not limit the scope of the claims attached hereto. Additionally, any examples set forth in this specification are not intended to be limiting and merely set forth some of the many possible embodiments for the appended claims.

The present disclosure is generally related to reactors or reaction systems, in particular, fermentors and fermentation systems. Fermentors are generally defined as any vessel in which a fermentation process is carried out. Given the vast number of fermentation processes and the wide variety of fermentable substrates, fermentors can range from simple continuous stirred tank reactors to highly complex, specialized systems having gas distribution and internal structures tailored to a particular substrate and/or a particular biological species. Fermentors useful in converting carbon-containing gases to larger biomolecules generally disperse a gas substrate within a liquid medium containing one or more nutrients to provide a multi-phase reaction mixture. This multi-phase reaction mixture is fed to one or more microbiological organisms that convert the gas substrate to larger biomolecules through metabolism. The gas substrates, nutrients, and microbiological organisms comprising the colony (i.e., the biomass within the fermentor) can be variously adjusted or tailored to provide a desired product, which may be present as a liquid, gas, or intracellular material. Fermentors according to the present disclosure are particularly useful in converting a gas substrate containing $CO_2$ to protein-rich biomass product, e.g., biomass with relatively high proportions of proteins.

As used herein, the term "microorganism" refers to any microorganism or microbial culture having the ability to use one or more gaseous substrates as a source of carbon or energy or as its sole source of energy and carbon, and may or may not use other carbon substrates (such as sugars, proteins, lipids and complex carbohydrates) for energy and carbon. Preferably, the microorganisms used herein is capable of converting $CO_2$ into biomass and protein-rich biomass. Example of microorganism include at least one the following genera: *Acidithiobacillus* sp.; *Acidovorax* sp.; *Alcaligenes* sp.; *Anabaena* sp.; *Ankistrodesmus* sp.; *Aquificae* sp.; *Bradyrhizobium* sp.; *Chlamydomonas* sp.; *Cupriavidus* sp.; *Derxia* sp.; *Flavobacteriae* sp.; *Gordonia* sp.; *Helicobacter* sp.; *Hydrogenobacter* sp.; *Hydrogenomonas* sp.; *Hydrogenophaga* sp.; *Hydrogenothermaceae* sp.; *Hydrogenovibrio* sp.; *Mycobacteria* sp.; *Nocardia* sp.; *Pseudomonas* sp.; *Ralstonia* sp.; *Renobacter* sp.; *Rhaphidium* sp.; *Rhizobium* sp.; *Rhodococcus* sp.; *Thiocapsa* sp.; *Variovorax* sp.; *Xanthobacter* sp.; and combinations thereof.

The microorganisms or microbial cultures used herein may also include a chemo-autotrophic microorganism selected from the following genera: *Acetoanaerobioum* sp.; *Acetobacerium* sp.; *Acetogenium* sp.; *Achronobacater* sp., *Acidianus* sp.; *Acinetobacer* sp.; *Actinomadura* sp.; *Aeromonas* sp.; *Alcaligenes* sp.; *Alcaligenes* sp.; *Arcobacter* sp.; *Aureobacterium* sp.; *Bacillus* sp.; *Beggiatoa* sp.; *Butyribacterium* sp.; *Carboxydothermus* sp.; *Clostridium* sp.; *Comamonas* sp.; *Dehalobacter* sp.; *Dehalococcoide* sp.; *Dehalospirillum* sp.; *Desulfobacterium* sp.; *Desulfomonile* sp.; *Desulfotomaculum* sp.; *Desulfovibrio* sp.; *Desulfursarcina* sp.; *Ectothiorhodospira* sp.; *Enterobacter* sp.; *Eubacterium* sp.; *Ferroplasma* sp.; *Halothibacillus* sp.; *Hydrogenobacter* sp.; *Hydrogenomonas* sp.; *Leptospirillum* sp.; *Metallosphaera* sp.; *Methanobacterium* sp.; *Methanobrevibacter* sp.; *Methanococcus* sp.; *Methanosarcina* sp.; *Micrococcus* sp.; *Nitrobacter* sp.; *Nitrosococcus* sp.; *Nitrosolobus* sp.; *Nitrosomonas* sp.; *Nitrosospira* sp.; *Nitrosovibrio* sp. *Nitrospina* sp.; *Oleomonas* sp.; *Paracoccus* sp.; *Peptostreptococcus* sp.; *Planctomycetes* sp.; *Pseudomonas* sp.; *RalsOntia* sp.; *Rhodobacter* sp.; *Rhodococcus* sp.; *Rhodocyclus* sp.; *Rhodomicrobium* sp.; *Rhodopseudomonas* sp.; *Rhodospirillum* sp.; *Shewanella* sp.; *Streptomyces* sp.; *Sulfobacillus* sp.; *Sulfolobus* sp.; *Thiobacillus* sp.; *Thiomicrospira* sp.; *Thioploca* sp.; *Thiosphaera* sp.; *Thiothrix* sp.; *and combinations thereof.*

If desired, the systems and processes described herein may be performed using microorganisms genetically modified so as to generate a desired chemical compound which can then be extracted from the intercellular fluid or the biomass harvested from the reactor. The scientific and patent literature contains numerous examples of such genetically modified microorganisms.

In particular, the present disclosure provides systems and methods for recycling gas in a reactor (or fermentor of fermentation system or the like). The gas can be a gas substrate introduced into the reactor, or a gas intermediate or product generated in the reaction or fermentation process within the reactor, or a gas separated from a liquid medium within the reactor, or a mixture thereof. The present gas-recycling systems and methods may be implemented in a reactor or fermentor. For example, the present gas-recycling system or components thereof may be installed on or integral with a reactor. Alternatively, the present-recycling system may itself provide a substantial part or framework for a reactor.

Some embodiments of the gas-recycling systems and methods described herein provide one or more possible advantages described below. Gas substrate that is introduced to the reactor that implements the present gas-recycling system is allowed to recirculate in the reactor without substantial release, thereby significantly improving efficiency of gas conversion and overall yield of biomass production. The gas-recycling system could improve the mixing efficiency of gas with the liquid medium; prolong the contact time of gas with the fermentation broth holding the microorganisms; increase the contact area of gas with the fermentation broth holding the microorganisms in the heterogeneous reaction mixture; improve mass transfer efficiency within the reactor; and/or maximize a pump efficiency of the reactor. Moreover, the gas-recycling system could substantially reduce waste and gas emission. In particular, the $CO_2$, $O_2$ and hydrogen introduced to the reactor is recycled and reused without substantial emission, which could maximize the conversion yield of $CO_2$ and hydrogen thereby saving energy and benefit the environment. Further, reactors that employ the present gas-recycling system may advantageously allow users to avoid high agitation or shear forces applied to the reaction mixture in the reactors and to save energy and cost. Additionally, implementation of the present gas-recycling system may allow to keep the microorganisms intact or protect the microorganisms from being destroyed by high shear force, ease harvest of biomass during downstream processing, keep the biomass product intact, and/or enable production of single-cell protein.

Figure 1B:
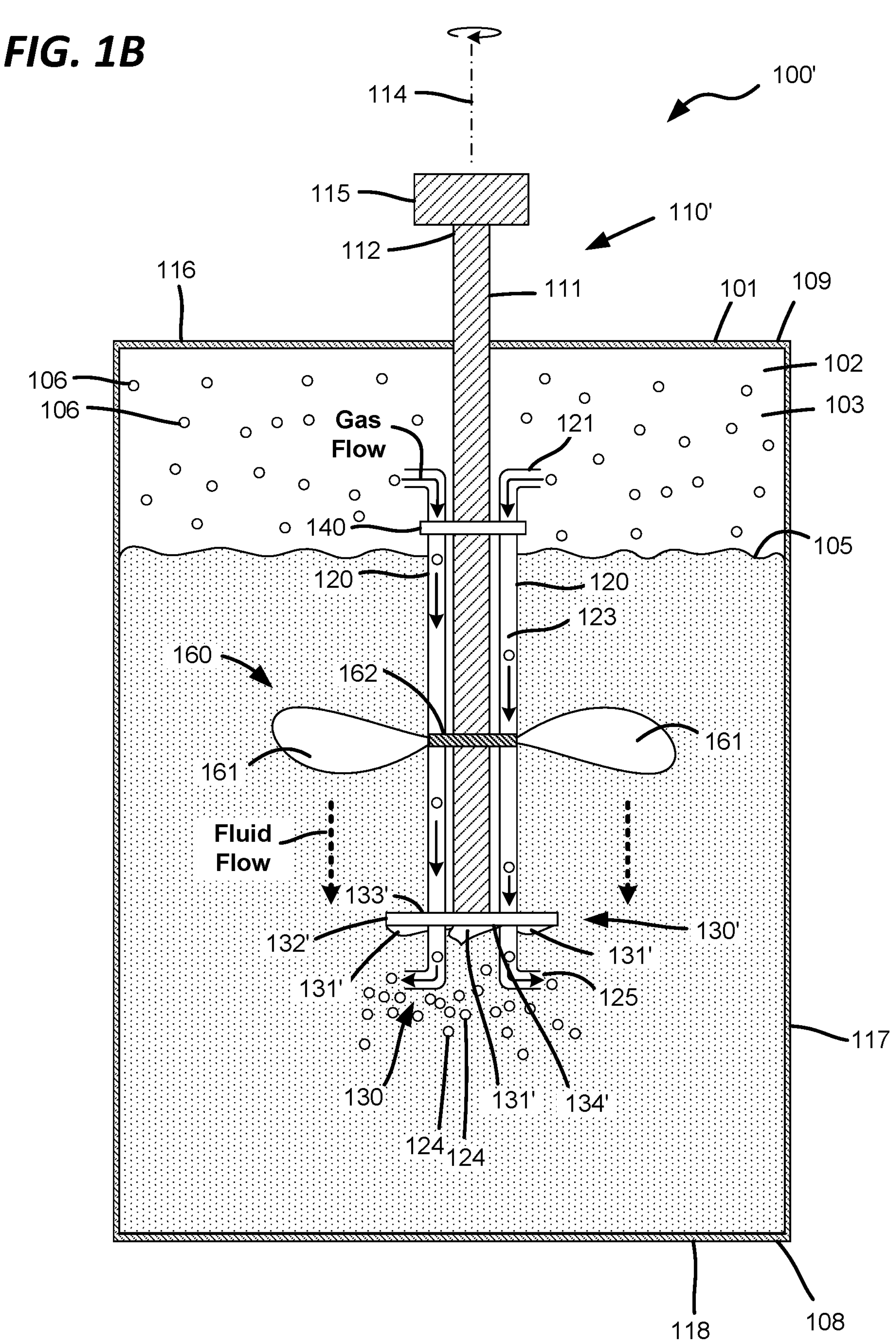
FIG. 1B illustrates a schematic view of another example gas-recycling system 100'.
Figure 1C:
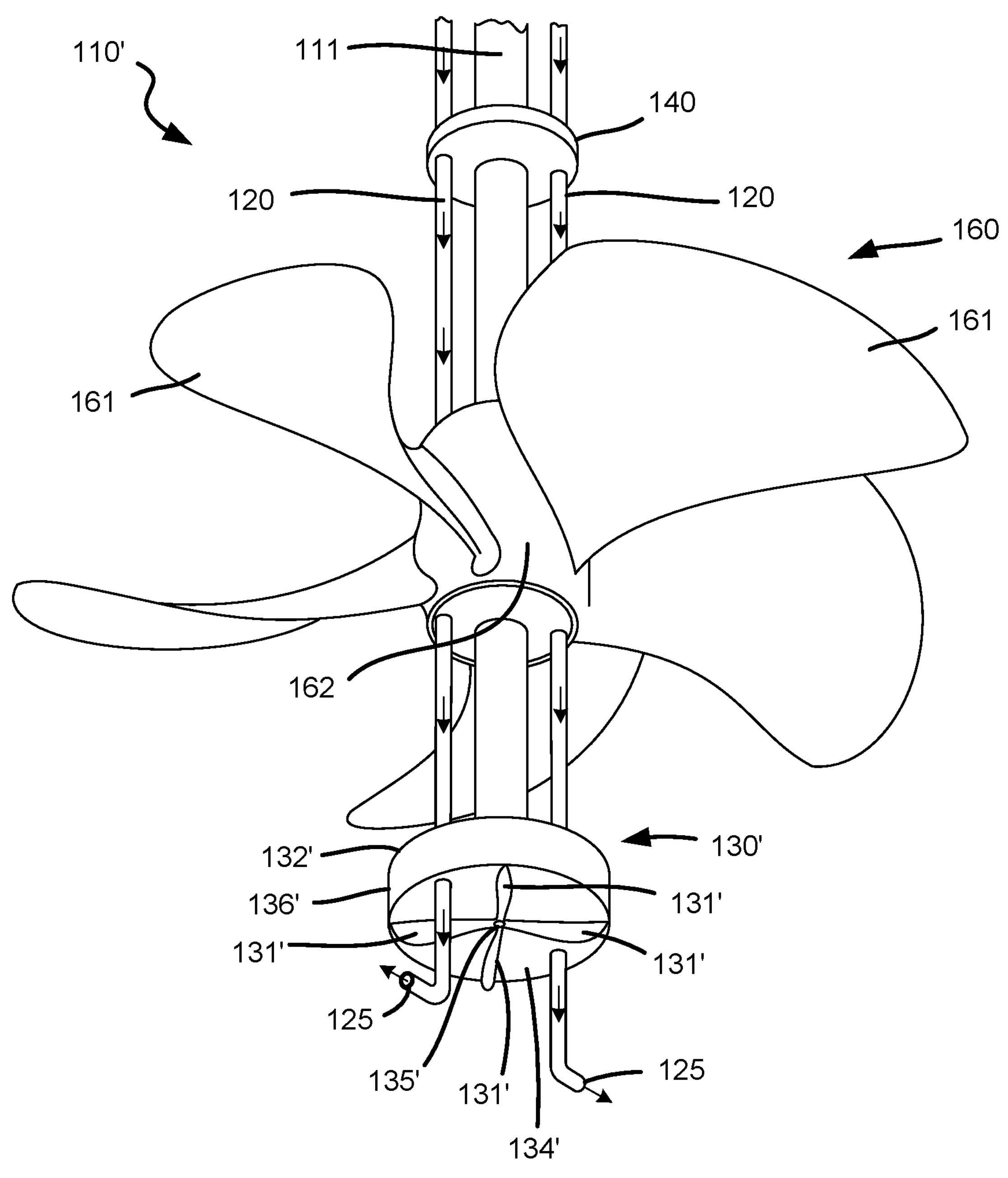
FIG. 1C illustrates an isometric view of at part of the gas-recycling system 100' of FIG. 1B.

Now referring to FIGS. 1A-1C, examples of the present gas-recycling system and various aspects thereof will be illustrated and described. FIG. 1A is a schematic diagram of a general gas-recycling system 100. In the illustrated example, the gas-recycling system 100 includes a housing 101, a powered propeller 110, and a gas conduit 120. The housing 101 may be a housing of a reactor or fermentor and in a substantially vertical position relative to the ground level. The housing 101 may extend from a top end 109 downwardly to a bottom end 108 along a central axis 114, and may further include a top wall 116, a bottom wall 118, and a continuous side wall 117 that circumstantially connects to the top wall 116 and the bottom wall 118. The housing may be substantially closed and enclose an internal space 102 comprising a gas space 103 and a liquid space 104. The gas space 103 takes an upper portion of the internal space 102 and is configured to collect and contain a gas 106 produced in the internal space 102. The gas 106 may comprise a gas substrate that has been introduced into the housing 101 from an external source, or a gas by-product generated from a reaction or fermentation process in the housing 101, or a gas that is separated from a liquid medium 107 within the housing 101, or a mixture thereof. The liquid space 104 takes a lower portion of the internal space 102 and is configured to contain a liquid medium 107 within the housing 101. The gas space 103 and the liquid space 104 are separated by a gas-liquid interface 105. The volume of the gas space 103 and the liquid space 104 may be adjusted by the amount of liquid medium 107 and operating conditions of the gas-recycling system 100.

The powered propeller 110 includes a rotatable shaft 111, a motor 115, and a suction-generating device 130. The shaft 111 extends from an upper end 112 to a lower end 113 along the central axis 114 of the housing 101. The upper end 112 may extend out of the housing 101. The lower end 113 extends into the liquid space 104. A distance between the lower end 113 of the shaft 111 and the bottom wall 118 of the housing 101 may be adjustable. The motor 115 is operably connected to the upper end 112 of the shaft 111 and provides power to drive rotation of the shaft 111 about the central axis 114.

The gas conduit 120 extends from a first open end 121 to a second open end 122 along the central axis 114 within the housing 101. The first open end 121 is within the gas space 103 and is in gas communication therewith, and the second open end 122 is within the liquid space 104 and is in gas communication therewith. In some embodiments, the gas conduit 120 comprises a plurality of openings 125 at the second open end 122. The openings are proximate and slightly elevated in position relative to the lower end 113 of the shaft 111. The gas conduit 120 includes an interior space 123 that allows a gas to pass therethrough in a downward direction from the first open end 121 to the second open end 122 without obstruction. The gas is allowed to exit the gas conduit 120 through the openings 125 and be reintroduced into the liquid space 104 and mixed with the liquid medium 107. In a preferred embodiment, the gas conduit 120 and the shaft 111 are concentric, and the shaft 111 extends through the interior space 123 of the gas conduit 120, forming a gap (G) therebetween. The diameter of the shaft 111, the diameter of the gas conduit 120, and the gap G are adjustable.

The suction-generating device 130 is operably connected to the lower end 113 of the shaft 111 and is proximate the openings 125 of the gas conduit 120. The suction-generating device 130 is configured to generate a suction and apply the suction to the gas conduit 120 to cause the gas 106 to flow from the gas space 103 to the liquid space 104 through the gas conduit 120 within the housing 101. In some embodiments, the suction-generating device 130 is a Venturi unit. The Venturi unit used herein is an apparatus or device that can cause a Venturi effect, which is the reduction in pressure that results when a fluid flows through a constricted section of the Venturi unit. Because of the proximity of the Venturi unit 130 with the second open end 122 of the gas conduit 120, the reduced pressure induces a suction that may cause the gas 106 in the gas space 103 to flow through the gas conduit 120 and enter the liquid medium 107 in the liquid space 104. In a particular embodiment, the Venturi unit comprises a plurality of blades 131, each blade operably connected to the lower end 113 of the shaft 111. The blades 131 may each extend in a radially outward direction and have a blade gap 132 between every two adjacent blades. The blades 131 upon rotation about the central axis 114 effectively shear the liquid medium 107, which flows through the blade gap 132 and thereby generate a reduced pressure under the Venturi effect. In addition, the rotating blades 131 may further mix the liquid medium 107 and the gas 106 that is reintroduced into the liquid medium 107.

In some embodiments, the gas-recycling system 100 optionally includes a liquid pump 160 operably connected to the powered propeller 110. The liquid pump 160 is above the suction-generating device 130 and below the gas-liquid interface 105. The liquid pump 160 is configured to increase the pressure and flow of the liquid medium 107 and maintain the downward flow direction thereof. In some embodiments, the liquid pump 160 comprises an impeller. The impeller may be an open impeller, a semi-open impeller, or a closed impeller. In some embodiments, the impeller is a part of the powered propeller and includes a plurality of propeller blades 161 and an adaptor 162. The adaptor 162 is circumferentially connected to an exterior surface of the gas conduit 120 and fixed to the powered propeller 110 in relative position. The propeller blades 161 are each fixed onto the adaptor 162 and extend from the adaptor 162 outwardly to the side wall 117 in a radial direction relative to the central axis 114. Advantageously, the pump capacity of the liquid pump 160 is maintained high because of the low gas holdup in the liquid space 104 between the gas-liquid interface 105 and the suction-generating device 130.

During operation, the powered propeller 110 is driven by the motor 115 and controlled either automatedly or manually to rotate about the central axis 114 at a rotation speed. The shaft 111, the suction-generating device 130, and the liquid pump 160 may co-rotate about the central axis 114 conjunctively in the same direction and at the same rotation speed. Upon rotation, the powered propeller 110 is configured to perform at least one of the following functions: (1) generate a suction to cause the collected gas 106 to flow from the gas space 103 to the liquid space 104 through the gas conduit 120; (2) cause the liquid medium 107 to flow in a downward direction from the gas-liquid interface 105 to the bottom end 108; and (3) mix the liquid medium 107 and the gas 106 reintroduced into the liquid medium 107.

The suction force (reduction of pressure) generated by the powered propeller 110 depends on several factors including the rotation speed, the type and configuration of the suction-generating device, and the physical properties (temperature, velocity, viscosity) of the liquid. These factors can be controlled coordinately to achieve a desired suction force. The suction force causes the gas 106 to flow at a flow rate into the liquid medium 107. The flow rate is adjustable and depends on factors including the suction force, the size of gap G of the interior space 123, the size of the open ends 121 and 122.

The gas 106 reintroduced into the liquid medium 107 through the gas conduit 120 may form gas bubbles 124 below the lower end 113 of the shaft 111. In some embodiments, the suction-generating device 130 may be further configured to shear or break apart the gas bubbles 124, reduce the size of the gas bubbles 124, prevent coalescence, and thereby promote mixing of the gas bubbles 124 with the liquid. As such, both contact area and contact time of gas-liquid interaction within the gas-recycling system 100 can be significantly improved.

In one example implementation of the gas-recycling system 100, the rotating blades 131 are configured to produce Venturi effect and apply a suction to the gas conduit 120 to cause the gas 106 to flow from the gas space 103 to the liquid space 104 through the gas conduit 120. The rotating blades 131 are further configured to shear or break apart the gas bubbles 124, reduce the size of the gas bubbles 124, prevent coalescence, and thereby promote mixing of the gas bubbles 124 with the liquid. The liquid pump 160 or the propeller blades 161 are configured to cause the liquid medium 107 to flow downwardly and prevent or reduce backflow of gas bubbles 124.

Now referring to FIGS. 1B and 1C, another example gas-recycling system 100', as a variation of the of the gas-recycling system 100, will be illustrated and described. FIG. 1B is a schematic view of a gas-recycling system 100'; FIG. 1C is an isometric view of a part of the gas-recycling system 100' of FIG. 1B. In the illustrated example, the gas-recycling system 100' includes a housing 101, a powered propeller 110, at least one a gas conduit 120, a suction-generating device 130', and optionally a fixture 140 and a liquid pump 160. The housing 101, the powered propeller 110, the gas conduit 120, and the liquid pump 160 are described above and will not be repeated here unless otherwise indicated.

In the illustrated example, the gas-recycling system 100' includes at least one gas conduit 120 proximate and external to the shaft 111 along the central axis 114. In some embodiments, the gas-recycling system 100' includes a plurality of gas conduits 120 surrounding at least a portion of the shaft 111, and each gas conduit 120 is proximate and external to the shaft 111 aligned with the central axis 114.

In the illustrated example, the suction-generating device 130' includes a base 132' and a plurality of blades 131'. The base 132' extends from a center 135' to a circumference 136' in a radial direction relative to the central axis 114. The base 132' has a top surface 133' and a bottom surface 134'. The top surface 133' is connected to the lower end 113 of the shaft 111 at or proximate the center 135'. The plurality of blades 131' are connected to the bottom surface 134' and aligned radially relative to the central axis 114. Each blade 131' extends in a direction from the center 135' to the circumference 136' and is apart from each other. In some embodiments, the suction-generating device 130' may include at least 2, at least 3, at least 4, at least 5, at least 8, or at least 12 blades. Each blade 131' may be a fluid shearing or mixing blade that is configured to generate Venturi effect to induce and apply a suction to the at least one gas conduit 120, as described above.

The at least one gas conduit 120 may extend through the base 132' between every two adjacent blades 131'. The at least one gas conduit 120 has a first open end located and in gas communication with the gas space 103 and a second open end 122 located and in gas communication with the liquid space 104. The second open end 122 include at least one opening 125 allowed for the gas in the gas conduit 120 to enter into the liquid space 104. The opening 125 of the at least one gas conduit 120 may be proximate the bottom surface 134' of the base 132'.

In some embodiments, the gas-recycling system 100' optionally includes a fixture 140 connected to the at least one gas conduit 120 and the shaft 111. As illustrated, the at least one gas conduit 120 and the shaft 111 may each extend through the fixture 140 with their relative position fixed by the fixture 140. During operation, the fixture 140 allows the at least one gas conduit 120 and the shaft 111 to co-rotate about the central axis 114 in a conjunctive manner in the same direction and at the same rotation speed.

In some embodiments, the gas-recycling system 100' optionally includes a liquid pump 160 operably connected to the shaft 111. Similar to the gas-recycling system 100, the liquid pump 160 is below the gas-liquid interface 105 and configured to increase the pressure and flow of the liquid medium 107 and maintain the downward flow direction thereof. In some embodiments, the liquid pump 160 comprises an impeller having a plurality of propeller blades 161 and an adaptor 162. The adaptor 162 is circumferentially connected to an exterior surface of the shaft 111 and fixed to the powered propeller 110' in relative position. The propeller blades 161 are each fixed onto the adaptor 162 and extend from the adaptor 162 outwardly to the side wall 117 in a radial direction relative to the central axis 114.

In one example implementation of the gas-recycling system 100', the shaft 111, the at least one gas conduit 120, the fixture 140, the suction-generating device 130, and the liquid pump 160 co-rotate about the central axis 114 conjunctively in the same direction and at the same rotation speed. The suction-generating device 130' is configured to produce Venturi effect and apply a suction to the at least one gas conduit 120 to cause the gas 106 to flow from the gas space 103 to the liquid space 104 through the at least one gas conduit 120. The rotating blades 131' are configured to shear or break apart the gas bubbles 124, reduce the size of the gas bubbles 124, prevent coalescence, and thereby promote mixing of the gas bubbles 124 with the liquid. The liquid pump 160 or the propeller blades 161 are configured to cause the liquid medium 107 to flow downwardly and prevent or reduce backflow of gas bubbles 124.

The present disclosure also provides reactors (or fermentors or fermentation systems or the like) that implement any gas-recycling system described herein. The reactor provided herein may have various configurations, including but not limited to, tank or vessel reactor, or loop reactor.

Figure 2:
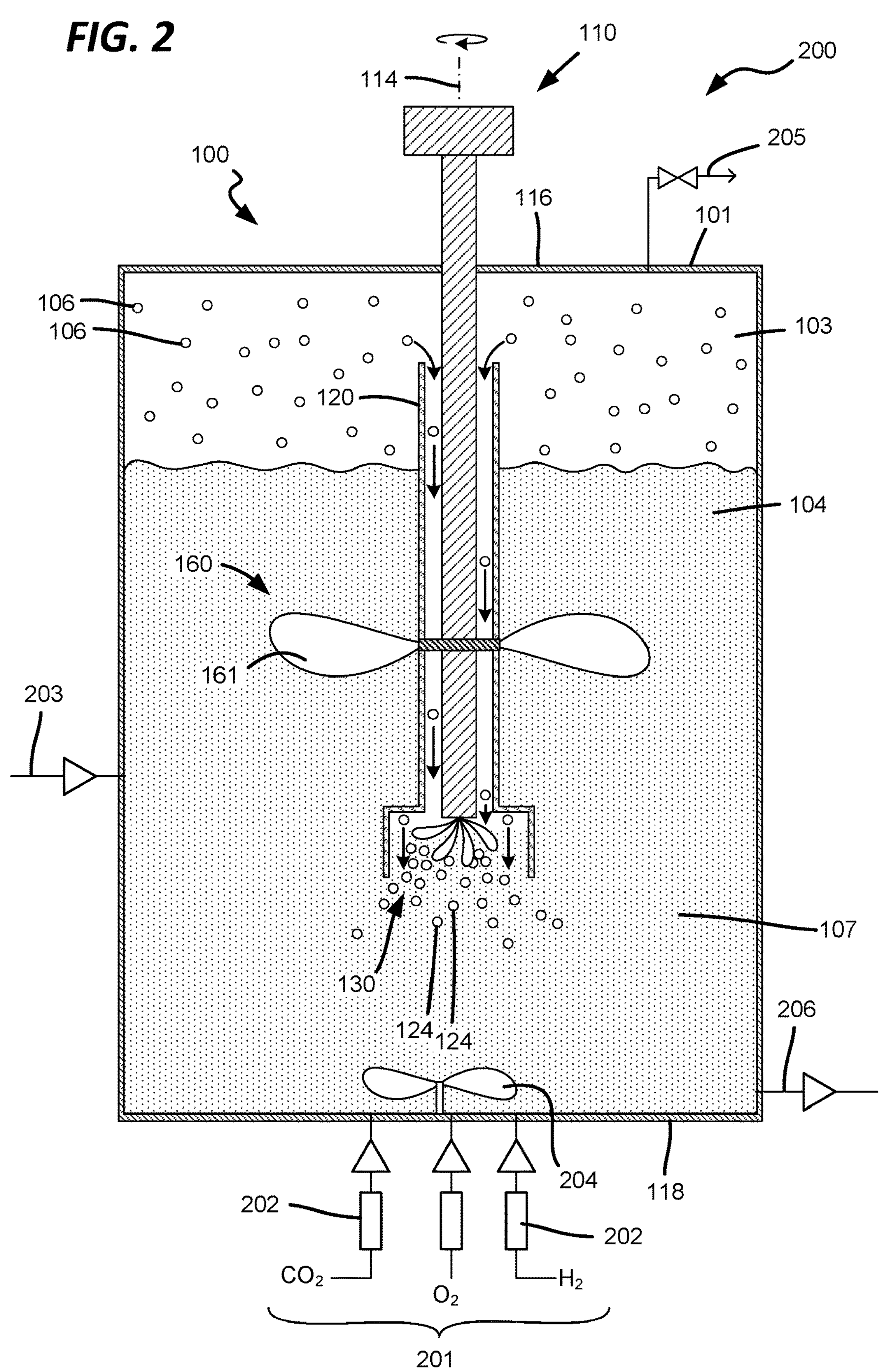
FIG. 2 illustrates a schematic view of a first example reactor comprising the gas-recycling system of FIG. 1.
Figure 3:
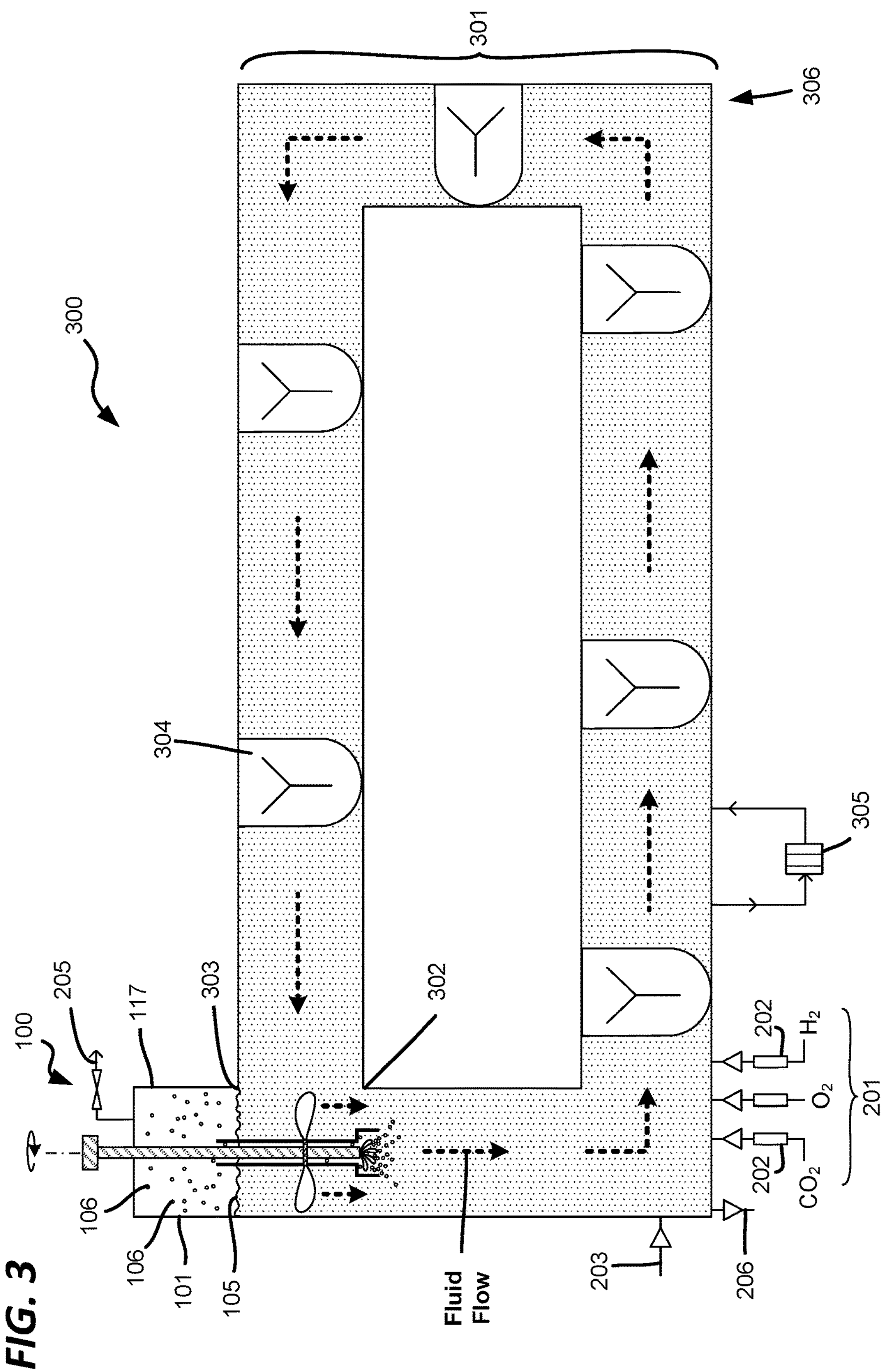
FIG. 3 illustrates a schematic view of a second example reactor comprising the gas-recycling system of FIG. 1.
Figure 4:
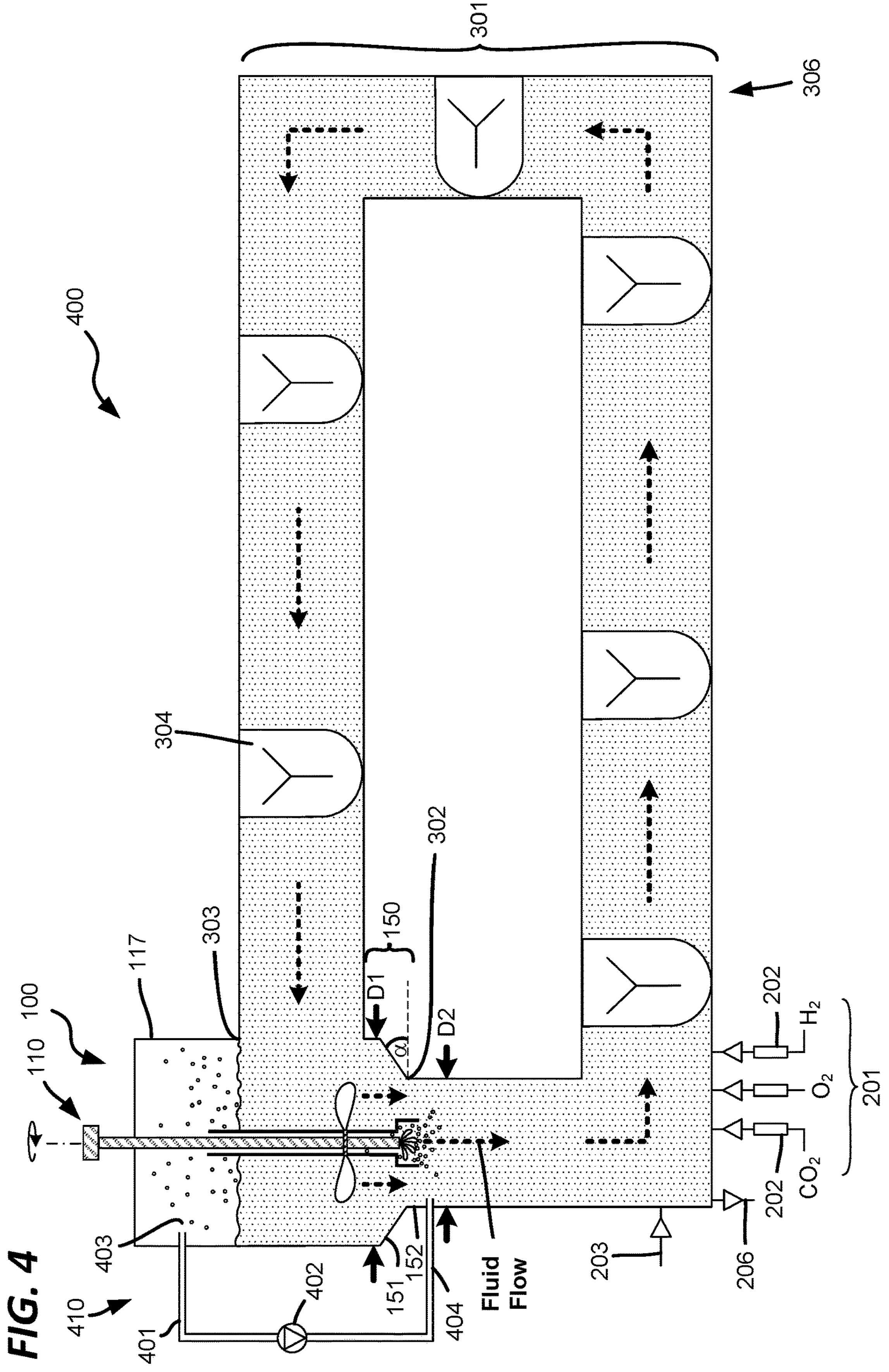
FIG. 4 illustrates a schematic view of a third example reactor comprising the gas-recycling system of FIG. 1.

Now referring to FIGS. 2-4, particular examples of the reactor will be illustrated and described. FIG. 2 is a schematic view of a tank reactor. In the illustrated example, the tank reactor 200 includes the gas-recycling system 100 or 100' as a substantial framework of the tank reactor 200, at least one gas inlet 201, at least one liquid medium inlet 203, at least one outlet 206, and optionally a gas controller 202 connected to the gas inlet 201, at least one mixer 204, and a pressure controller 205. Various aspects of the gas-recycling system 100 or 100' are described above and will not be repeated here unless otherwise indicated.

In some embodiments, the tank reactor 200 is configured to produce biomass via a fermentation process within the tank reactor. The liquid space 104 may include a reaction mixture comprising a gas substrate and the liquid medium 107. The gas substrate may include $CO_2$, $H_2$, $O_2$, and optionally $N_2$. In some embodiments, the gas substrate further include a $C_1$ substrate such as $CH_4$, CO, a syngas ($CO+H_2$), a natural gas, or combinations thereof. The liquid medium 107 includes water, one or more nutrients, and one or more microorganism or microbial culture described herein. The nutrients include ingredients capable of supporting or transporting dissolved or suspended sustenance to biomass forming microbiological organisms in the multiphase reaction mixture within the tank reactor 200 and promoting microorganism growth. The nutrients may include ammonia or salts or derivatives thereof, phosphate (e.g. as phosphoric acid), minerals such as magnesium, calcium, potassium, iron, copper, zinc, manganese, nickel, cobalt and molybdenum, sulphates, chlorides, or nitrates. The microorganism may be of any type according to the present disclosure. In a particular embodiment, the microorganism or microbial culture in the liquid medium 107 is capable of converting $CO_2$ into biomass, in particular, protein-rich biomass.

The tank reactor 200 may include at least one gas inlet 201 connected to and in gas communication with the tank reactor 200. In one embodiment, the gas inlet 201 is connected to the bottom wall 118 of the tank reactor 200. In another embodiment, the gas inlet 201 is connected to the side wall 117 of the tank reactor 200 and is in gas communication with the gas space 103. The at least one gas inlet 201 is configured to introduce at least one input gas substrate into the tank reactor 200. The input gas substrate my include $CO_2$, $H_2$, $O_2$, and optionally $N_2$, a $C_1$ substrate such as $CH_4$, CO, natural gas, a syngas ($CO+H_2$), or combinations thereof. In one particular embodiment, at least one gas inlet 201 is operably connected to a source of $CO_2$, which is configured to supply $CO_2$ to the tank reactor 200. The source of $CO_2$ may be from an industrial process such as a flue gas (exhaust gas or stack gas), a combustion plant that generates a $CO_2$-rich gas, or a fermentation process that generates $CO_2$ from microbiol culture (e.g., yeasts, *coli, Bacillus, Streptococcus, Lactobacillu, Escherichia, Salmonella, Corynebacterium*), or an industrial farming process that generates biogenic $CO_2$ from metabolism of living aquatic animals (e.g., fish) in a farming plant, or a natural resource such as air or water.

In some embodiments, the tank reactor 200 further includes a gas controller 202 operably connected to the each of the gas inlet(s) 201. The gas controller 202 is configured to adjust the ratio of the input gas substrates to a described level (e.g., in metabolic stoichiometry) before introduction to the tank reactor 200. The input gas substrate(s) may be combined and mixed to form a homogenous gas mixture before introduction to the tank reactor 200. Alternatively, the input gas substrate(s) may be separated introduced into the tank reactor 200 without mixing.

The tank reactor 200 may include a liquid medium inlet 203 configured to introduce the liquid medium 107 or any nutrients thereof to the tank reactor 200.

The gas space 103 is configured to collect and contain the gas 106 introduced to and/or generated in the tank reactor 200. The gas 106 may include water vapor, unconsumed gas substrates, gas by-products generated in the fermentation process, and combinations thereof. The gas 106 of the gas space 103 is recycled and reintroduced into the liquid medium 107 through use of the gas-recycling system 100, and thereby recirculate in the tank reactor 200 as described above. In some embodiments, the tank reactor is closed during operation without gas exchange with the atmosphere and without substantially release of the gas 106 out of the tank reactor 200.

The tank reactor 200 may further include at least one mixer 204 (e.g., an impeller) configured to stir the reaction mixture within the housing 101 and promote mixing of the gas, nutrient, and microorganism in the reaction mixture of the liquid medium 107. In some embodiments, the mixer 204 is fixed on an interior surface of the bottom wall 118 and is configured to rotate about the central axis 114 at the same direction with the powered propeller 110 during operation. In some embodiments, the mixer 204 is fixed on an interior surface of the side wall 117. In some embodiments, the tank reactor comprises at least one mixer 204 operably attached to the extended shaft 111 and configured to co-rotate with the shaft 111 conjunctively during operation.

The tank reactor 200 further includes an outlet 206 configured to allow the produced microorganisms from the fermentation process to be removed from the tank reactor 200. The collected microorganisms can be further processed to recover desired biomass products. In some instances, the microorganisms collected via the outlet 206 can be introduced to a separation subsystem (not shown) for processing and recovery of desired products. The biomass products may be further processed to produce a feed product that can be supplied to aquatic organisms in industrial fermentation plants or aquatic farming plants.

The tank reactor 200 may optionally include a pressure controller 205 configured to control the pressure of the tank reactor for safety consideration and/or for improving gas mass transfer during operation. The pressure controller 205 may further comprise a gas relief unit common in the art.

FIG. 3 is a schematic view of one example loop reactor 300. This reactor design allows gas mixture to be richer in $O_2$ with no risk in explosion, thus increasing productivity of biomass and conversion efficiency of gas substrates. In the illustrated example, the loop reactor 300 includes a loop section 301 and a gas-recycling system 100 or 100' that is integral to the loop section 301. Various aspects of the gas-recycling system 100 or 100' are described above and will not be repeated unless otherwise indicated.

The loop section 301 includes an upstream end 302 and a downstream end 303. The upstream end 302 is integrally connected to the housing 101 at the bottom end 108 thereof. The downstream end 303 is integrally connected to the side wall 117 of the housing 101. The upstream end 302 is in fluid communication with the housing 101, such that the liquid medium 107 can flow from the housing 101 to the loop section 301 through the upstream end 302 without physical obstruction. In some embodiments, the upstream end 302 is circumferentially connected to the side wall 117 of the housing 101 at the bottom end 108 thereof, and no bottom wall 118 is needed. The downstream end 303 is in fluid communication with the housing 101, such that the liquid medium 107 flows from the loop section 301 into the housing 101 through the downstream end 303 without physical obstruction. The size (e.g., diameter of the housing 101) of the gas-recycling system 100 or 100' may be substantially the same with the size (or diameter) of the loop section 301, such that the gas-recycling system 100 or 100' may be viewed as an integral segment of the loop reactor 300. In such configuration, the gas space 103 may be viewed as a "headspace" of the loop reactor 300.

During operation, the liquid medium 107 recirculates in the loop reactor in a flow direction from the liquid space 104 of the housing 101 downwardly to the upstream end 302, through the loop section 301 to the downstream end 303, and back to the housing 101. The gas 106 also recirculates in the loop reactor 300 in the flow direction similar to the liquid medium 107. In particular, the gas 106 collected in the gas space 103 flows downwardly into the liquid medium 107 through use of the powered propeller 110. The liquid medium 107 carrying the gas 106 flows through the loop section 301 and back into the housing 101, where a portion of the gas 106 is separated from the liquid medium 107 at the gas-liquid interface 105 and flows back into the gas space 103. In some embodiments, the loop reactor 300 is substantially closed during operation, without substantial release of the gas 106 out of the loop reactor 300.

As described above, the gas-recycling system 100 and 100' may include a liquid pump 160 in the liquid space 104 between the gas-liquid interface 105 and the suction-generating device 130. The liquid pump 160 is configured to maintain the downward flow direction of the liquid medium 107 in the liquid space 104. The loop reactor 300 allows the gas to be enriched in the gas space (headspace) 103 and the loop section 301, thereby minimizing gas holdup in the liquid medium within the liquid space 104. As a result, the pump capacity of the liquid pump 160 may be improved and maintained high.

The loop section 301 may further include one or more of the following components: at least one gas inlet 201, at least one gas controller 202, a liquid medium inlet 203, a pressure controller 205, and an outlet 206, the various aspects of which have been described above and will not be repeated here unless otherwise indicated.

The loop section 301 may further include at least one static mixer 304, positioned along the length of loop section 301. Benefits of the use of static mixers are described in U.S. Pat. No. 7,579,163 and include mixing of the gases into the multi-phase reaction mixture. Exemplary types of static mixers are also described in the '163 patent. Static mixers that can be used in embodiments described are not limited to those described in the '163 patent. Static mixers other than those described in the '163 patent can be used in the embodiments described herein. For example, other types of static mixers are available from companies such as StaMixCo LLC of Brooklyn, N.Y. and Sulzer Management Ltd. of Winterthur, Switzerland. In some embodiments, as many as 100 static mixers 304 may be used in the loop reactor 300. The static mixers 304 may be provided at a density of at least one mixer per three meters of the loop section 301 when the static mixer has a length of about 1 meter. In some embodiments, static mixers are spaced apart by a distance about equal to 1-3 times the length of one of the static mixers. In some embodiments, fewer or greater numbers of static mixers can be provided and the static mixers may be provided at a lesser or greater density. The particular number of static mixers used and the density at which they are deployed will be determined in part based upon their contribution to mass transfer of gas into the liquid and microorganisms and/or the pressure drop produced by the static mixers. In a particular embodiment, the loop section 301 comprises a plurality of static mixers 304 at a density of about one mixer per one meter distributed along a majority of the loop section 301, with fewer or no static mixer in a segment closer to the downstream end 303 to allow the gas bubbles in the loop section 301 to coalesce, rise, and released into the gas space 103.

In some embodiments, the loop reactor further include a heat transfer unit operation 305 operably connected to the loop section 301. The heat transfer unit operation 305 is configured to introduce or remove thermal energy from the multi-phase reaction mixture in the loop section 301. The heat transfer unit operation 305 can introduce thermal energy to or remove thermal energy from the multi-phase mixture in the loop section 301 at one or more locations along loop section 301. In at least some instances, the microbiological activity that occurs within the loop reactor 300 generates heat as a byproduct. Left uncontrolled, such heat can adversely affect the metabolism or health of the microbiological organisms within the loop reactor 300. Alternatively, microbiological organisms may also have a temperature below which the metabolism or health of the organism is adversely affected. As such, the biological organisms within the loop reactor 300 have a defined temperature range providing optimal growth and metabolic conditions. In at least some instances, the multi-phase reaction mixture within the loop reactor 300 can be maintained at a temperature of about 130° F. or less; about 120° F. or less; about 110° F. or less; about 100° F. or less; about 95° F. or less; about 90° F. or less; about 85° F. or less; or about 80° F. or less using the heat transfer unit operation 305. In at least some instances, the multi-phase reaction mixture within the loop reactor 300 can be maintained at a temperature of from about 55° F. to about 120° F.; about 60° F. to about 110° F.; about 110° F. to about 120° F.; about 100° F. to about 120° F.; about 65° F. to about 100° F.; about 65° F. to about 95° F.; or about 70° F. to about 90° F., using heat transfer unit operation 305.

In some embodiments, the loop section 301 may have a U-shaped configuration, including two elbow portions 306 that bend at about 90° angles when viewed from above. The loop section 301 may take other shapes. For example, loop section 301 may include more than the two 90° elbow portions 306 or may include more than one elbow portion 306 that is less than 90°. In other embodiments, loop section 301 can include a plurality of elbow portions 306 that are greater than 90° or less than 90°.

The loop section 301 may be substantially planar. In some embodiments, the loop section 301 is substantially co-planar with the housing 101 and is substantially vertical relative to the ground level. Alternatively, the loop section 301 may be substantially horizontal relative to the ground level.

In some embodiments, the loop reactor 300 does not have a pressure reduction device or a pressure reduction zone common in the art. The pressure of the liquid medium within the loop section 301 may be controlled at a constant profile, without an intentional reduction of pressure near the downstream end 303. The gas-liquid separation occurs naturally within the housing 101 without external assistance (e.g. an intended reduction of pressure). With the contribution of the gas-recycling system 100, the gas 106 is maximally remained in the liquid medium 107 and recirculates in the loop reactor 300, which advantageously improves the mass transfer efficiency.

FIG. 4 is a schematic view of another example loop reactor 400, which is a variation of the loop reactor 300. Similar to the loop reactor 300, the loop reactor 400 includes a loop section 301 and a gas-recycling system 100 or 100' that is integral to the loop section 301. Various aspects of the gas-recycling system 100 or 100' and the loop section 301 are described above and will not be repeated here unless otherwise indicated.

In the illustrated example of FIG. 4, the housing 101 of the gas-recycling system 100 or 100' further includes a bottom portion 150 that is in a "funnel-like" configuration with a sloped side wall 151 and a narrowed bottom end 152. The upstream end 302 of the loop section 301 is integrally connected to the narrowed bottom end 152 and is in fluid communication with the housing 101. In particular, the sloped side wall 151 of the bottom portion 150 is circumferentially connected to the side wall 117, and is circumferentially connected to the loop section 301 at the upstream end 302. The sloped side wall 151 may be sloped in an angle $\alpha$ from about 0 to about 80 degree relative to the ground level. In some embodiments, the narrowed bottom end 152 and the upstream end 302 may be substantially the same in size or diameter. The lower end 113 of the shaft 111 may extend into the bottom portion 150 or further into the loop section 301 at or proximate the upstream end 302 thereof.

In a preferred embodiment, the housing 101 has a diameter D1 that is larger than the diameter D2 of the bottom end 152 or the upstream end 302. The ratio of D1 to D2 may be adjustable, e.g., at least about 1.2, at least about 1.5, at least about 2, at least about 3, at least about 4, at least about 5, or at least about 10. Such size restriction may advantageously allow the loop reactor 400 to generate a Venturi effect that may provide additional suction to recycle the gas 106. In one embodiment, during operation, the liquid medium 107 flows from the housing 101 through the "funnel-like" bottom portion 150 into the loop section 301 that is restricted in size, thereby generating a reduced pressure under the Venturi effect that may cause the gas 106 to flow through the gas conduit 120 into the liquid medium 107.

In another embodiment, the powered propeller 110 or 110' upon rotation generates a suction to recycle the gas 106 in the gas space 103 into the liquid medium 107, and the liquid medium 107 flows through the bottom portion 150 and the upstream end 302 generates an additional suction that further promotes recycling of the gas 106.

In yet another embodiment, the loop reactor 400 further includes an external gas-recycling system 410 configured to provide an additional passageway to recycle the gas 106 and/or to improve the recycling efficiency. In some embodiments, the external gas-recycling system 410 includes an external gas conduit 401 and a gas compressor 402 operatively connected to the external gas conduit 401. The external gas conduit 401 has a first end 403 and a second end 404. The first end 403 is connected to the housing 101 and is in gas communication with the gas space 103. The second end 404 is connected to the bottom portion 150 or the loop section 301 proximate the upstream end 302, and is in gas communication with the liquid medium 107. The gas compressor 402 is configured to pump the gas 106 to flow through the external gas conduit 401 into the liquid medium 107 proximate the upstream end 302. When operating together with the powered propeller 110 or 110', the loop reactor 400 may improve gas recycling efficiency and gas mass transfer efficiency.

The reactor described in the present disclosure may be operated with an adjustable flow control device (not shown) set for different flow rates of the gas and/or liquid medium through the adjustable flow control device. Steady state conditions, such as volumetric pump output, temperature of multi-phase reaction mixture, fluid and/or gas pressure, dissolved gas content of multi-phase mixture, volumetric flow rate of $CO_2$ into the loop section, volumetric flow rate of $O_2$ into the loop section, volumetric flow rate of $H_2$ into the loop section, volumetric flow rate of $N_2$ into the loop section, and/or pH of multi-phase reaction mixture within the reactor may vary. The liquid medium 107 may have a pH from about 4 to about 9, or from about 5 to about 8, or from about 6 to about 7. The liquid medium may have a density of the multi-phase mixture from about 1.0 $kg/m^3$ to about 2 $kg/m^3$.

Figure 5:
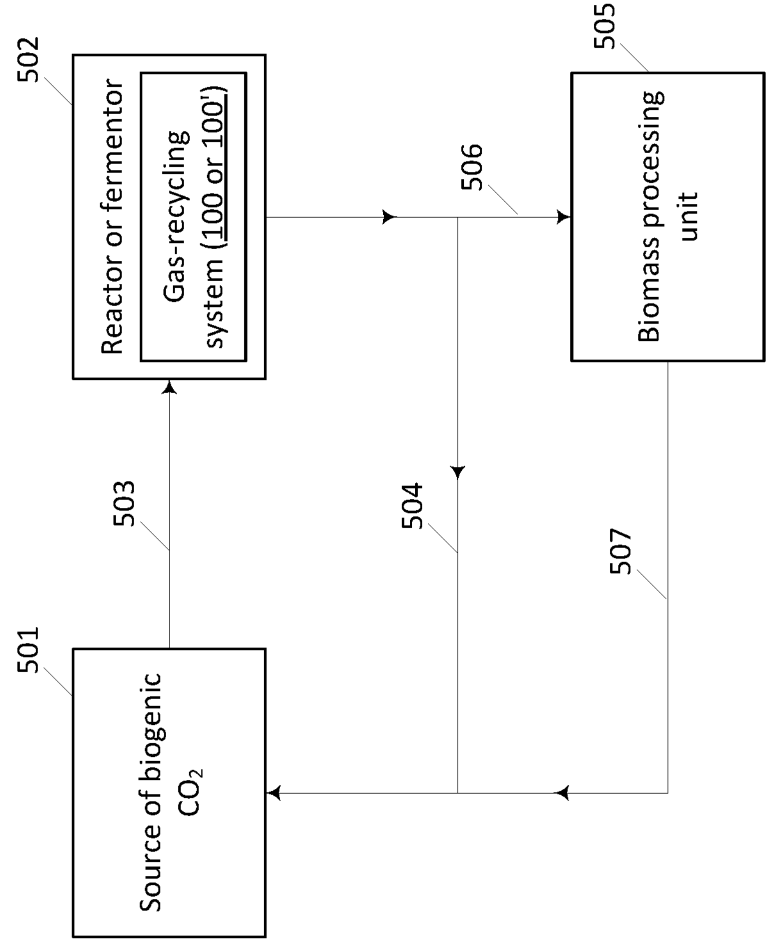
FIG. 5 illustrates a schematic view of one example system comprising a reactor of any one of FIGS. 2-4.

Now referring to FIG. 5, one example of a system for producing biomass will be illustrated and described. In the illustrated example, the system 500 includes a source of biogenic $CO_2$ 501 and a reactor or fermentor 502. The source 501 is in connection with the reactor 502 via a supply line 503 and a feed line 504. The supply line 503 is configured to transport the biogenic $CO_2$ from the source 501 to the reactor 502. The feed line 504 is configured to transport biomass or feed that is produced in the reactor 502 to the source 501. The source of biogenic $CO_2$ 501 may be an aquatic farming plant that cultivates aquatic animals such as fish in the plant or a fermentation plant that cultivates microorganisms as described above. The aquatic animals or fermentation microorganisms produce biogenic $CO_2$ through metabolism. The biogenic $CO_2$ may be collected and optionally processed (e.g., through purification, filtration, or condensation) before supplying to the reactor 502.

The reactor or fermentor 502 may be any reactor described herein, including the tank reactor 200, the loop reactor 300 or 400, or a reactor comprising the gas-recycling system 100 or 100' according to the present disclosure. The reactor 502 includes a liquid medium that has a microorganism capable of converting $CO_2$ into biomass via a fermentation process within the reactor, as described herein. The produced biomass product may be directly supplied to the source 501 via the feed line 504 as a feed for the living animals or fermentation microorganism therein. In some embodiments, the system 500 further includes a biomass processing unit 505 in connection with the reactor 502 and the source of biogenic $CO_2$ 501 via a supply line 506 and a feed line 507 respectively. The biomass processing unit 505 is configured to receive the biomass product from the reactor 502; process and formulate the biomass product to produce a feed product; and supply the feed product to the source 501 for feeding the aquatic animals or fermentation microorganisms therein.

In some embodiments, the system 500 is substantially closed, and the biogenic $CO_2$ from the source 501 recirculates in the system 500, and is at least partially reused and recycled through operation of the gas-recycling system 100 or 100' of the reactor 502, without substantial release to the environment.

Figure 6:
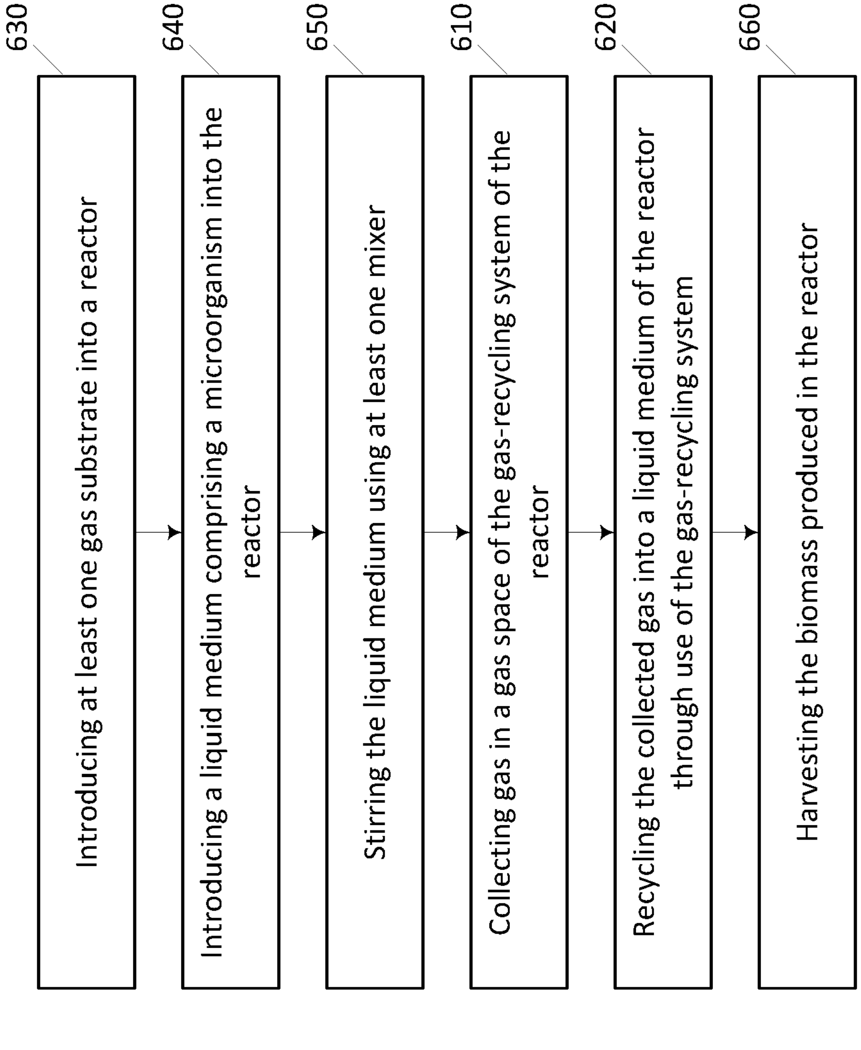
FIG. 6 illustrates a flow diagram of one example method for recycling gas in a reactor.

Now referring to FIGS. 6-8, example methods for recycling gas in a reactor and/or for producing biomass in a reactor will be illustrated and described. FIG. 6 is a flow diagram of one example method 600 for recycling gas in a reactor. The reactor of the method 600 may be a tank reactor 200, a loop reactor 300 or 400, or any other type of reactor that includes a gas-recycling system 100 or 100' according to the present disclosure. The method 600 includes operation 610 and 620. At 610, gas is collected in the gas space 103 of the gas-recycling system 100 or 100'. The gas may include gas substrates introduced into the housing 101, gas by-products generated in the housing 101, or gas separated from the liquid medium 107, or any combinations thereof. At 620, the powered propeller 110 is operated to rotate about the central axis 114 to recycle at least a part of the gas 106 from the gas space 103 to the liquid medium 107 through the gas conduit 120, according to the present disclosure.

In some embodiments, the reactor is a loop reactor 400 and further includes an external gas-recycling system 410 according to the present disclosure. The method 600 may further include activating the gas compressor 402 to cause at least a part of the gas to flow from the gas space 103 into the liquid medium 107 through the external gas conduit 401.

The method 600 may optionally include operation 630. At 630, at least one gas substrate is introduced into the reactor via at least one gas inlet 201. The gas substrate may include $CO_2$, $H_2$, $O_2$, $N_2$, or any mixture thereof. In some embodiments, the $CO_2$ is supplied from a source of biogenic $CO_2$ that is in direct or indirect connection with the reactor.

The method may optionally include operation 640. At 640, a liquid medium such as a microorganism culture medium is introduced into the reactor via at least one liquid medium inlet 203. The liquid medium may include a microorganism capable of converting $CO_2$ into biomass. In some embodiments, a liquid is introduced into the reactor at 640 and allowed to slowly mix with the gas substrate in the reactor. Microorganisms are subsequently introduced into the reactor and combined with the liquid and gas to form a reaction mixture. The microorganism are allowed to grow in the reaction mixture by converting the gas substrate that is introduced to and recycled in the reactor into biomass.

The method may optionally include operation 650. At 650, the liquid medium is stirred by at least one static mixer (e.g., the mixer 204 or static mixer 304) to promote mixing of the reaction mixture.

The method may optionally include operation 660. At 660, the produced biomass within the reactor is collected and removed from the outlet 206. The removed biomass may be supplied to an aquatic farming for feeding the aquatic animals therein. Alternatively, the biomass may be further processed and formulated to produce a feed product that is supplied to the aquatic farming plant.

In some embodiments, the method 600 allows to recycle the gas in the reactor, without substantial emission to atmosphere during operation.

FIG. 7 is a flow diagram of one example method 700 for producing biomass. In the illustrated example, the method 700 includes operations 710, 720, 730, 740, and 750. Operation 710 includes culturing a microorganism in a reaction mixture that recirculates in a reactor, wherein the reaction mixture comprises a liquid medium and gas, and wherein the microorganism is capable of converting the gas into biomass. The reactor may be a tank reactor or a loop reactor, according to the present disclosure.

Operation 720 includes introducing at least one gas substrate from an external source into the liquid medium. Operation 730 includes collecting gas in a gas space within the reactor. Operation 740 includes recycling the collected gas back to the liquid medium. In some embodiments, operations 730 and 740 are performed through use of a gas-recycling system 100 or 100' and/or an external gas-recycling system 410 according to the present disclosure. Accordingly, operation 730 may include operation 610, and operation 740 may include operation 620, as described above. Operation 750 includes harvesting the biomass from the reactor. Operation 750 may include operation 660 as described above.

The method 700 may optionally include an operation 760. At 760, the gas within the reactor is prevented from substantially releasing into atmosphere during operation. As such, the method 700 allows the gas to recirculate in the reactor.

FIG. 8 is a flow diagram of one example method 800 for recycling $CO_2$ and producing biomass from $CO_2$. In the illustrated example, the method 800 includes operations 810, 820, 830, 840, and 850. Operation 810 includes culturing a microorganism in a reaction mixture that recirculates in a reactor, wherein the reaction mixture comprises a liquid medium and a gas comprising $CO_2$, and wherein the microorganism is capable of converting $CO_2$ into biomass. Operation 820 includes introducing a gas substrate comprising $CO_2$ from an external source into the liquid medium. In some embodiments, $CO_2$ gas is supplied from a source of biogenic $CO_2$ connected to the reactor via a supply line.

Operation 830 includes collecting at least a part of the $CO_2$ separated from the liquid medium within the reactor. Operation 840 includes recycling the collected $CO_2$ back to the liquid medium. Operations 830 and 840 may be performed through use of a gas-recycling system 100 or 100' and/or an external gas-recycling system 410 according to the present disclosure. Operation 850 includes harvesting the biomass from the reactor.

The method 800 may optionally include operations 860 and 870. At 860, the produced biomass is supplied to the source of biogenic $CO_2$ for feeding the aquatic organisms therein. At 870, the produced biomass is further processed and/or formulated to produce a feed product that is supplied to the source of biogenic $CO_2$ for feeding the aquatic organism, in accordance with the system 500 described above.

When introducing elements of the present disclosure or the various versions, embodiment(s) or aspects thereof, the articles "a", "an," "the," and "said" are intended to mean that there are one or more elements. The terms "comprising," "including," and "having" are intended to be inclusive and mean that there may be additional elements other than the listed elements.

The term "about" is used here in conjunction with numeric values to include normal variations in measurements as expected by persons skilled in the art, and is understood to have the same meaning as "approximately" and to cover a typical margin of error, such as 15% of the stated value.

"Fermentation" is defined as "a metabolic process that produces chemical changes in organic substrates through the action of enzymes. For the purposes of this disclosure, "fermentation" is a process for cultivating cells in a specialized containers, tanks, vessel, or reactors (made of glass, metal or plastic and known as a fermenter or fermentor or fermentation tank or bio-reactor) under controlled process conditions in order to optimize their growth and maximize efficiency. The controlled process conditions include sterility, temperature, pressure, agitation rate, pH, input gas composition and flow rate, nutrient composition, cell density, dissolved gas concentration, biomass removal rate (for continuous or semi-continuous harvesting) and the like. Fermentation may be aerobic or anaerobic.

"Gas fermentation" refers to a fermentation in a fermentation tank or a bioreactor, wherein the metabolic processes of microorganisms or microbes or cells extract energy and carbon from the gaseous inputs that are supplied to them. Gas fermentation can refer to anaerobic or aerobic process of microbe cultivation on gases. By combining these gas inputs with the simple inorganic salts in the medium, chemo-autotrophic cells convert these basic inputs into more complex biomass and other cellular products. Gas fermentation can be either aerobic or anaerobic, depending on the organism used and the feedstock gases available for fermentation. Gas fermentation is a particularly advantageous form of chemo-autotrophic fermentation because the key inputs are provided by widely available gases such as $CO_2$, $H_2$, $O_2$, $CH_4$, etc.

"Cultivating" is defined as meaning "the act or process of culturing living material (such as bacteria or yeasts) in a prepared nutrient medium." "Nutrient" is defined as meaning "a substance or ingredient that promotes growth, provides energy, and maintains life." "Medium" is defined as "a nutrient system for the artificial cultivation of cells or organisms and especially bacteria." Media can be liquid, semi-solid or solid (e.g., agar, beads, or other scaffolding). Solid or semi-solid media can provide a growth support for the cells.

"Chemo-autotrophic" is defined as "being auto trophic and oxidizing an inorganic compound as a source of energy." The inorganic compound as a source of energy may include $H_2$, in the case of hydrogen-oxidizing microorganism, which can consume a combination of $CO_2$, $H_2$, and $O_2$. Examples include anaerobic acetogens that consume $CO_2$ for carbon and $H_2$ for energy. Chemoautotrophic metabolism is known in bacteria and archaea, and may also exist as an undiscovered trait, or as a capability conferred by genetic modification, in some other organisms. Examples of chemoautotrophs are found across numerous bacterial genera including but not limited to *Cupriavidus, Rhodobacter, Methylobacterium, Methylococcus, Methylosinus, Nitrosomonas, Nitrosococcus, Nitrobacter, Nitrococcus, Paracoccus, Hydrogenothermus, Hydrogenovibrio, Clostridium, Rhodococcus, Rhodospirillum, Alcaligines, Rhodopseudomonas*, and *Thiobacillus*, as well as in a number of genera of the archaea, including methanogens. Specific examples of chemoautotrophs include *Cupriavidus necator, Cupriavidus basilensis, Rhodococcus opacus, Methylococcus capsulatus, Methylosinus trichosporium, Methylobacterium extorquens, Hydrogenothermus marinus, Rhodospirillium rubrum, Rhodopseudomonas palustrus, Paracoccus zeaxanthinifaciens, Rhodobacter sphaeroides, Rhodobacter capsulatus*, and *Clostridium autoethanogenum*.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A gas-recycling system for recycling gas in a loop-shaped reactor, the gas-recycling system comprising:

an enclosure including a loop section, enclosing an internal space comprising a gas space and a liquid space, wherein the liquid space includes liquid, and wherein the gas space is configured to collect gas separated from the liquid space within a reactor;

a liquid pump arranged in the liquid space to increase or maintain pressure and flow direction in the liquid space and prevent or reduce backflow of gas bubbles in the liquid space; and a powered propeller comprising:

a shaft having an upper end and a lower end, wherein the lower end extends into the liquid space;

a plurality of blades connected to the lower end of the shaft; and a gas conduit extending from a first end to a second end, wherein the first end is in gas communication with the gas space, and wherein the second end is proximate the radial blades and extending into the liquid space;

wherein upon rotation of the powered propeller, the powered propeller is configured to:

generate a suction to cause the collected gas to flow from the gas space to the liquid space through the gas conduit; and mix the liquid and the collected gas proximate the powered propeller.

2. The gas-recycling system of claim 1, wherein the reactor is a fermentation reactor.

3. The gas-recycling system of claim 1, wherein the reactor causes fluid therein to flow through the loop section by the liquid pump.

4. The gas-recycling system of claim 1, wherein the gas conduit is within the enclosure, and wherein a part of the shaft extends through an interior space of the gas conduit.

5. The gas-recycling system of claim 1, further comprising an external gas conduit external to the enclosure, and wherein the gas-recycling system further comprises a gas compressor connected to the external gas conduit, the gas compressor configured to promote gas flow from the gas space to the liquid space.

6. The gas-recycling system of claim 1, wherein the liquid pump comprises a plurality of propeller blades connected to the powered propeller above the lower end of the shaft, wherein the propeller blades are configured to co-rotate conjunctively with the shaft during operation.

7. The gas-recycling system of claim 1, wherein the liquid space contains a reaction mixture comprising:

gaseous substrates comprising $CO_2$, or derived dissolved carbon compounds, $H_2$, and $O_2$;

nitrogen and phosphorus-comprising compounds and other minerals required to sustain growth of microorganisms; and microorganisms capable of converting the substrate into biomass.

8. The gas-recycling system of claim 7, wherein the microorganism is a knallgas microorganism selected from the group consisting of: *Rhodopseudomonas* sp., *Rhodospirillum* sp., *Rhodococcus*; sp., *Rhizobium* sp.: *Thiocapsa* sp., *Pseudomonas* sp., *Nocardia* sp., *Hydrogenomonas* sp., *Hydrogenobacter* sp., *Hydrogenovibrio* sp.: *Helicobacter* sp., *Xanthobacter* sp., *Hydrogenophaga* sp., *Bradyrhizobium* sp., *Ralstonia* sp., *Gordonia* sp.: *Mycobacteria* sp., *Alcaligenes* sp.: *Cupriavidus* sp.: *Variovorax* sp., *Acidovorax* sp., *Anabaena* sp.: *Scenedesmus* sp.: *Chlamydomonas* sp., *Ankistrodesmus* sp., *Rhaphidium* sp., and combinations thereof.

9. The gas-recycling system of claim 7, wherein the reactor further comprises one or more inlets configured to introduce $CO_2$, $H_2$, $O_2$ or any combinations thereof into the reactor.

10. The gas-recycling system of claim 9, wherein the external $CO_2$ gas being introduced into the reactor is from a source of biogenic $CO_2$.

11. The gas-recycling system of claim 10, wherein the source of biogenic $CO_2$ comprises an aquatic farming plant, wherein the biogenic $CO_2$ is produced by living aquatic organisms therein.

12. The gas-recycling system of claim 11, wherein the produced biomass from the reactor is supplied to the aquatic farming plant as feed.

13. The gas-recycling system of claim 9, wherein the external $CO_2$ gas being introduced into the reactor is generated from an industrial process or an industrial fermentation process.

14. The gas-recycling system of claim 7, further comprising a controller configured to adjust the ratio of the $CO_2/H_2/O_2$ being introduced into the reactor.

15. The gas-recycling system of claim 7, wherein the reactor further comprises an exit port configured to harvest the produced biomass from the reactor.

16. The gas-recycling system of claim 11, wherein the loop section further comprises a plurality of static mixers configured to promote the mixing of the gas into the liquid medium.

17. The gas-recycling system of claim 1, wherein the liquid pump is driven by the shaft of the powered propeller.

18. A fermentation reactor comprising:

an enclosure including a loop section, enclosing an internal space comprising a gas space and a liquid space, wherein the liquid space includes liquid, and wherein the gas space is configured to collect gas separated from the liquid space within a reactor;

a liquid pump arranged in the liquid space to increase or maintain pressure and flow direction in the liquid space and prevent or reduce backflow of gas bubbles in the liquid space; and a powered propeller comprising:

a shaft having an upper end and a lower end, wherein the lower end extends into the liquid space;

a plurality of blades connected to the lower end of the shaft; and a gas conduit extending from a first end to a second end, wherein the first end is in gas communication with the gas space, and wherein the second end is proximate the blades and extending into the liquid space;

wherein upon rotation of the powered propeller, the powered propeller is configured to:

generate a suction to cause the collected gas to flow from the gas space to the liquid space through the gas conduit; and mix the liquid and the collected gas proximate the powered propeller.

19. A loop-shaped reactor comprising:

an enclosure including a loop section, enclosing an internal space comprising a gas space and a liquid space, wherein the liquid space includes liquid, and wherein the gas space is configured to collect gas separated from the liquid space within a reactor;

a liquid pump arranged in the liquid space to increase or maintain pressure and flow direction in the liquid space and prevent or reduce backflow of gas bubbles in the liquid space; and a powered propeller comprising:

a shaft having an upper end and a lower end, wherein the lower end extends into the liquid space;

a plurality of blades connected to the lower end of the shaft; and a gas conduit extending from a first end to a second end, wherein the first end is in gas communication with the gas space, and wherein the second end is proximate the blades and extending into the liquid space;

wherein upon rotation of the powered propeller, the powered propeller is configured to:

generate a suction to cause the collected gas to flow from the gas space to the liquid space through the gas conduit; and mix the liquid and the collected gas proximate the powered propeller, wherein the loop reactor causes fluid therein to flow from the lower portion of the liquid space to the upper portion of the liquid space through the loop section.

20. A process for recycling gas in a loop-shaped reactor, the process comprising:

collecting gas separated from a liquid space in a gas space within an enclosure of a gas-recycling system, the gas recycling system comprising:

an enclosure including a loop section, enclosing an internal space comprising a gas space and a liquid space, wherein the liquid space includes liquid, and wherein the gas space is configured to collect gas separated from the liquid space within a reactor;

a liquid pump arranged in the liquid space to increase or maintain pressure and flow direction in the liquid space and prevent or reduce backflow of gas bubbles in the liquid space; and a powered propeller comprising:

a shaft having an upper end and a lower end, wherein the lower end extends into the liquid space;

a plurality of blades connected to the lower end of the shaft; and a gas conduit extending from a first end to a second end, wherein the first end is in gas communication with the gas space, and wherein the second end is proximate the blades and extending into the liquid space;

rotating the powered propeller to:

generate a suction to cause the collected gas to flow from the gas space to the liquid space through the gas conduit; and mix the liquid and the collected gas proximate the powered propeller.

21. A process for producing biomass, the process comprising:

culturing a microorganism in a reaction mixture in a reactor, wherein the reaction mixture comprises a liquid medium, wherein the microorganism is capable of converting $CO_2$ into biomass;

introducing a substrate from an external source into the liquid medium and mixing the substrate with the liquid medium, wherein the substrate comprises $CO_2$, $H_2$, or $O_2$;

recycling gas separated from a liquid space back into the liquid space within the reactor, the reactor comprising:

an enclosure including a loop section, enclosing an internal space comprising a gas space and a liquid space, wherein the liquid space includes liquid, and wherein the gas space is configured to collect gas separated from the liquid space within a reactor;

a liquid pump arranged in the liquid space to increase or maintain pressure and flow direction in the liquid space and prevent or reduce backflow of gas bubbles in the liquid space; and a powered propeller comprising:

a shaft having an upper end and a lower end, wherein the lower end extends into the liquid space;

a plurality of blades connected to the lower end of the shaft; and a gas conduit extending from a first end to a second end, wherein the first end is in gas communication with the gas space, and wherein the second end is proximate the blades and extending into the liquid space;

collecting gas separated from the liquid space in the gas space;

rotating the powered propeller to:

generate a Venturi suction to cause the collected gas to flow from the gas space to the liquid space through the gas conduit; and mix the liquid and the collected gas proximate the powered propeller; and harvesting the biomass produced from the reactor.

* * * * *